US009078619B2

(12) United States Patent
Panasyuk et al.

(10) Patent No.: US 9,078,619 B2
(45) Date of Patent: Jul. 14, 2015

(54) HYPERSPECTRAL/MULTISPECTRAL IMAGING IN DETERMINATION, ASSESSMENT AND MONITORING OF SYSTEMIC PHYSIOLOGY AND SHOCK

(75) Inventors: Svetlana V. Panasyuk, Lexington, MA (US); Jenny E. Freeman, Weston, MA (US); Michael J. Hopmeier, Mary Esther, FL (US); Alexander A. Panasyuk, Lexington, MA (US); Brian H. Tracey, Arlington, MA (US)

(73) Assignee: Hypermed Imaging, Inc., Greenwich, CT (US)

( * ) Notice: Subject to any disclaimer, the term of this patent is extended or adjusted under 35 U.S.C. 154(b) by 0 days.

(21) Appl. No.: 11/319,225

(22) Filed: Dec. 28, 2005

(65) Prior Publication Data
US 2007/0024946 A1 Feb. 1, 2007

Related U.S. Application Data

(60) Provisional application No. 60/639,315, filed on Dec. 28, 2004, provisional application No. 60/639,282, filed on Dec. 28, 2004, provisional application No. 60/653,082, filed on Feb. 16, 2005, provisional application No. 60/653,081, filed on Feb. 16, 2005.

(51) Int. Cl.
*A61B 5/05* (2006.01)
*A61B 5/00* (2006.01)
(Continued)

(52) U.S. Cl.
CPC .............. *A61B 5/445* (2013.01); *A61B 5/0059* (2013.01); *A61B 5/0261* (2013.01);
(Continued)

(58) Field of Classification Search
CPC .... A61B 5/0059; A61B 5/489; A61B 5/0086; A61B 2019/5293; G01J 3/28
USPC ......... 600/310, 322, 323, 473, 407, 476–480; 356/301, 303, 317–320; 250/341.1
See application file for complete search history.

(56) References Cited

U.S. PATENT DOCUMENTS 5,772,593 A * 6/1998 Hakamata ................. 600/407
6,070,093 A 5/2000 Oosta et al.
(Continued)

FOREIGN PATENT DOCUMENTS

JP 2003505133 T 2/2003
WO WO 99/22640 5/1999
(Continued)

OTHER PUBLICATIONS

Murguia J. E. et al: "Compact Visible/near-infrared hyperspectral imager," Proceedings of the Spie—The International Society for Optical Engineering 2000 Spie—Int. Soc. Opt. Eng USA, vol. 4028, pp. 457-468.
(Continued)

*Primary Examiner* — Elmer Chao
(74) *Attorney, Agent, or Firm* — Brett A. Lovejoy; Andrew J. Antczak; Morgan, Lewis & Bockius, LLP

(57) ABSTRACT

The present invention provides a hyperspectral imaging system which demonstrates changes in tissue oxygen delivery, extraction and saturation during shock and resuscitation including an imaging apparatus for performing real-time or near real-time assessment and monitoring of shock, including hemorrhagic, hypovolemic, cardiogenic, neurogenic, septic or burn shock. The information provided by the hyperspectral measurement can deliver physiologic measurements that support early detection of shock and also provide information about likely outcomes.

23 Claims, 17 Drawing Sheets

(51) Int. Cl.

| | |
|---|---|
| *A61B 5/026* | (2006.01) |
| *A61B 5/1455* | (2006.01) |
| *G01J 3/02* | (2006.01) |
| *G01J 3/10* | (2006.01) |
| *G01J 3/28* | (2006.01) |
| *G01J 3/32* | (2006.01) |
| *G01N 21/31* | (2006.01) |
| *A61B 5/02* | (2006.01) |
| *A61B 5/029* | (2006.01) |
| *G01J 5/00* | (2006.01) |

(52) U.S. Cl.
CPC ............ *A61B 5/14552* (2013.01); *A61B 5/412* (2013.01); *A61B 5/416* (2013.01); *G01J 3/0224* (2013.01); *G01J 3/10* (2013.01); *G01J 3/2823* (2013.01); *G01J 3/32* (2013.01); *G01N 21/31* (2013.01); *A61B 5/0088* (2013.01); *A61B 5/02* (2013.01); *A61B 5/029* (2013.01); *A61B 5/7264* (2013.01); *G01J 2005/0077* (2013.01); *G01N 2021/3144* (2013.01); *G01N 2021/3155* (2013.01); *G01N 2201/0221* (2013.01); *G01N 2201/0627* (2013.01)

(56) References Cited

U.S. PATENT DOCUMENTS

| | | | |
|---|---|---|---|
| 6,487,440 | B2 | 11/2002 | Deckert et al. |
| 6,640,130 | B1* | 10/2003 | Freeman et al. ............. 600/474 |
| 6,650,916 | B2 | 11/2003 | Cook et al. |
| 2003/0052837 | A1 | 3/2003 | Raskar |
| 2003/0219207 | A1 | 11/2003 | Guy |
| 2004/0039269 | A1 | 2/2004 | Ward et al. |
| 2004/0039297 | A1 | 2/2004 | Abreu et al. |
| 2004/0111030 | A1* | 6/2004 | Zeman ........................... 600/473 |
| 2004/0116814 | A1 | 6/2004 | Stranc et al. |
| 2004/0215082 | A1 | 10/2004 | Chance |
| 2004/0236229 | A1* | 11/2004 | Freeman et al. ............. 600/474 |
| 2004/0240712 | A1 | 12/2004 | Rowe et al. |
| 2004/0249290 | A1 | 12/2004 | Shani et al. |
| 2005/0041244 | A1* | 2/2005 | Treado et al. ................. 356/301 |
| 2005/0273011 | A1 | 12/2005 | Hattery et al. |

FOREIGN PATENT DOCUMENTS

| | | |
|---|---|---|
| WO | WO 01/01854 | 1/2001 |
| WO | WO 01/06926 A1 | 2/2001 |
| WO | WO 01/54393 | 7/2001 |
| WO | WO 01/72216 | 10/2001 |
| WO | 03091729 | 11/2003 |
| WO | WO 2007/084099 | 7/2007 |

OTHER PUBLICATIONS

Zuzak K.J. et al.: "Noninvasive Determination of Spatially Resolved and Time-Resolved Tissue Perfusion in Humans During Nitric Oxide Inhibition and Inhalation by Use of a Visible-Reflectance Hyperspectral Imaging Technique" Circulation, vol. 104, 2001, pp. 2905-2910.

Cancio et al., "Visible hyperspectral imaging: monitoring the systemic effects of shock and resuscitation," *IEEE Proceedings of SPIE*, 2002 vol. 4614, pp. 159-168.

Gillies et al., "Systemic Effects of Shack and resuscitation Monitored by Bisible Hyperspectral Imaging," *Diabetes Technology & Therapeutics*, Jul. 5, 2004, vol. 5, No. 5, pp. 847-855.

EPO, Communication pursuant to Article 94(3) EPC dated Mar. 3, 2011 for application No. EP 05 857 613.3.

Yamaguchi, M. et al: "Multispectral Color Imaging for Dermatology: Application in Inflammatory and Immunologic Diseases" Thirteenth Color Imaging Conference: Color Science and Engineering Systems, Technologies, and Applications, vol. 13, Nov. 2005, p. 6PP, XP002621909 ISBN: 0-89208-259-3.

Zuzak K J et al: "Visible Reflectance Hyperspectral Imaging: Characterization of a Noninvasive, In Vivo System for Determining Tissue Perfusion" Analytical Chemistry, vol. 74, No. 9, 1 May 2002, pp. 2021-2028, XP001132716 American Chemical Society, US ISSN: 0003-2700 DOI: 10.1021/AC011275F.

Japanese Patent Office, Notice of Rejection with English translation dated Nov. 16, 2010 for Japanese patent application No. 2007-549525.

* cited by examiner

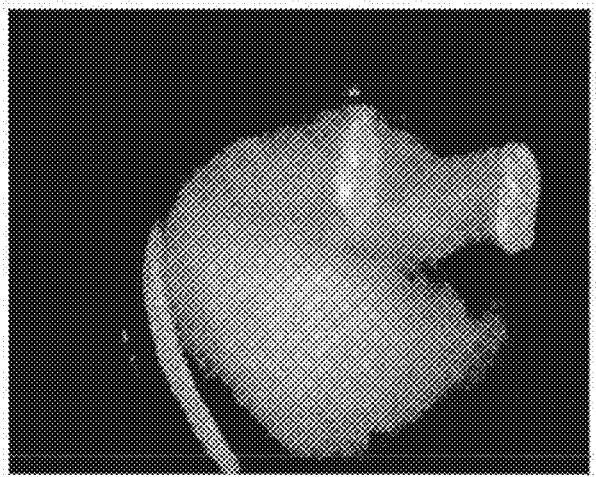
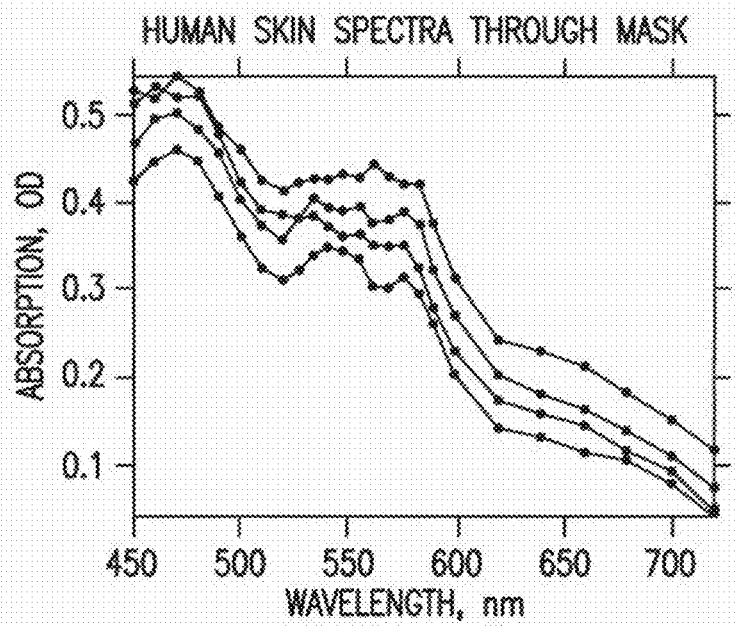
FIG. 15

HYPERSPECTRAL/MULTISPECTRAL IMAGING IN DETERMINATION, ASSESSMENT AND MONITORING OF SYSTEMIC PHYSIOLOGY AND SHOCK

REFERENCE TO RELATED APPLICATIONS

This application claims priority to U.S. Provisional Patent Application No. 60/639,315 entitled "Hyperspectral Imaging in Shock Prediction and Survivability Assessment" filed Dec. 28, 2004, U.S. Provisional Patent Application No. 60/639,282 entitled "Hyperspectral Imaging: A New Approach to the Diagnosis of Hemorrhagic Shock" filed Dec. 28, 2004, U.S. Provisional Patent Application No. 60/653,082 entitled "Hyperspectral Shock Index" filed Feb. 16, 2005, and U.S. Provisional Patent Application No. 60/653,081 entitled "Hyperspectral Vital Sign Monitor" filed Feb. 16, 2005, which are each hereby incorporated by reference in their entireties.

RIGHTS IN THE INVENTION

This invention was made, in part, with United States government support under funding by Technologies for Metabolic Monitoring 2002, DAMD 17-02-1-0714, and by the Combat Casualty Care Research Program, U.S. Army Medical Research and Material Command, and the United States government may have certain rights in the invention.

BACKGROUND

1. Field of the Invention

The invention is directed to a hyperspectral or multispectral imaging systems and apparatus for performing real-time and/or near real-time assessment and monitoring of one or more physiologic parameters. The invention is also directed to method of analyzing the hyperspectral and multispectral data to provide specific diagnoses and treatment options in, for example, shock and impending shock, hypovolemia, hemodynamic compromise, physiological derangement, dehydration, and hypothermia.

2. Description of the Background

Early detection of metabolic shock regardless of etiology is critical for a variety of civilian and military medical environments. Acute hemorrhage and subsequent circulatory collapse (shock) account for about 50% of the deaths on the battlefield and the forward operating table, a statistic that has remained relatively unchanged since World War I. In addition, hemorrhage is the primary cause of death in about 30% of injured soldiers who die from wounds. Likewise, uncontrolled hemorrhage accounts for up to 82% of the early operative deaths from trauma in the civilian arena. However, the mortality rate in combat casualties drops to 2% to 4% if the trauma patient is stabilized through surgery. It is therefore clear that the ability to provide an early diagnosis of shock significantly reduces mortality and morbidity associated with shock in both civilian and military settings.

Hemorrhagic shock is typically identified by the degree of hypotension, nonspecific signs and subjective symptoms such as cold clammy skin, pallor, weak thready pulse, unstable vital signs, and diminished mentation that develop as a result of blood loss. Similar symptoms are seen for other types of shock. The impact of shock is a mismatch between supply and demand leading to alterations in cellular metabolism in various tissues. All of these result from the insufficiency of the circulation to meet metabolic demands.

It is clear that past a certain point, shock becomes irreversible. For military applications, particularly in the battlefield, it is extremely useful to have indications as to which injured soldiers were expectant and which ought to be given therapy. Significant effort has been placed toward the delineation of criteria for predicting impending hemodynamic decompensation and for determining the irreversibility of shock in a variety of human and animal models. Similarly, information that could be used to assess other injury, exposure to chemical or biological agents, exhaustion, dehydration, nutritional state, level of mental or emotional stress, pharmacological agents, exposure to toxic agents such as carbon monoxide would be useful in both battlefield and civilian settings.

Adequate triage and diagnosis are key to appropriate application of potentially life saving therapeutic countermeasures. In the face of a chemical or biological exposure, it will be both critical and difficult to rapidly and accurately assess the hemodynamic status of wounded or affected individuals. Cumbersome chemical biowarfare (CBW) personal protective gear may prevent medical personnel or first responders from the access required for standard assessment of casualties who may also be wearing CBW gear. Taking a pulse or measuring blood pressure may be impossible. Any device placed in contact with a potentially contaminated individual may also be contaminated and may not be able to be reused without onerous cleansing measures or disposable covers. Therefore, the development and deployment of a remote sensing technology to provide physiologic and hemodynamic assessment in such circumstances would be highly advantageous. For maximum utility, such a technology would provide a hand-held, robust, turnkey system that could provide near-real time information. It would require minimal operator dexterity and would be operable by an end-user in CBW attire.

Profound acidosis, base deficit or rates of change of base deficit have all been associated with non-survivability, but it is well known that these occur late in the progression of shock. In addition, to date, the assessment of these parameters has required blood sample and laboratory equipment, which restricts the use of such tests for first responders. Other parameters such as profound hypotension or the onset of severe bradycardia or other significant dysrhythmias are often seen in shock immediately prior to a terminal event but cannot reliably provide sufficient advance notice to permit successful intervention. Milder degrees of hypotension or rhythm disturbances can be associated with either survival or death and offer no prognostic information. Thus, there is an outstanding need for monitoring devices that would provide earlier information about likely outcomes for a patient's response to shock.

Since the appearance of hypotension and reduced oxygen delivery reflect late events in the process of hemorrhagic shock, it is critical to identify physiological signals that are altered during the earliest time period of blood volume loss to provide an accurate assessment of the severity of shock. A common denominator in development of shock is inadequate oxygen delivery (DO2) to the tissue associated with reductions in blood flow (cardiac output) or metabolic alterations (reduced pH or base excess). Increased cardiac output and DO2 correlate well with survival while failure to stabilize cardiac output and DO2 is highly correlated with death. Therefore, approaches that include some indicator of oxygen delivery (e.g., stroke volume, cardiac output) represent better tools for the early prediction of circulatory shock than measurements currently used for this purpose.

SUMMARY

The present invention overcomes the problems and disadvantages associated with current strategies and designs and provides new tools and methods for assessing tissue oxygen saturation, oxygen delivery and oxygen extraction, and tissue hydration level of shock victims and other patients requiring physiological assessment in real-time or near real-time. This technology utilizes an assessment of local tissue by hyperspectral imaging to provide information about systemic physiology and disease state.

Accordingly, the invention is directed to hyperspectral and multispectral imaging systems, apparatus and methods for performing real-time or near real-time assessment and monitoring of one or more physiologic parameters including oxyhemoglobin, deoxyhemoglobin, water content, total hemoglobin and oxygen saturation that, when analyzed as described herein, provides metabolic and physiology status, such as, for example, the presence or evolution of shock, the adequacy of resuscitation or the potential for survival. Specific diagnoses derived from HSI data include shock, hypovolemia, hemodynamic compromise, physiological derangement, shock or impending shock state including hemorrhagic shock, hypovolemic shock, septic shock, cardiogenic shock, neurogenic shock, burn shock, dehydration, and hypothermia.

Microcirculatory changes similarly can be seen in chronic disease states such as diabetes or congestive heart failure. For example, hyperspectral measurement of tissue oxyhemoglobin and oxygen saturation ($S_{HSI}O_2$) was lower in the forearm of diabetic subjects with neuropathy even through this area is usually not affected by clinical somatic neuropathy (Greenman et al., Lancet 2005; 366: 1711). This observation involves hyperspectral imaging of a systemic microvascular change from a disease commonly targeted to the foot. Similar information provided by the hyperspectral measurement can support early detection of or additional information concerning shock or other physiological alterations, and also provide information about likely outcomes. Hyperspectral imaging using a hemorrhagic shock model in pigs and a low body negative pressure (LBNP) model in humans (human shock model that emulates a blood loss) demonstrated metrics that can be used to monitor and predict the onset of and recovery from shock. Embodiments of the device are useful in settings including, but not limited to, surgery, clinical procedures, health monitoring, emergency room or battlefield care, first response situations and medical evaluations in the field, hospital, and clinic or physician office. This technology evaluates (for the first time) local tissue in spatial, spectral, and temporal dimensions via hyperspectral imaging to provide information about systemic physiology and disease state.

One embodiment of the invention is directed to an apparatus to deliver MHSI images to diagnose and evaluate shock comprising a detector (e.g. camera), a controllable light source, a spectral separator, a power supply, and image acquisition and display hardware and an integrated analysis system comprised of hardware and software sufficient to convert data to usable information. The detector is preferably a digital camera, e.g. a camera having a charge-couple device (CCD) or a complementary metal oxide semiconductor (CMOS) detector, and a lens. Preferably, the light source is an array of light-emitting devices (e.g. light emitting diodes, LED) positioned around the light entry area to provide near-coaxial illumination, with intensity and duration for each controlled by a software program. Preferably, the spectral separator is a visible- or near-infrared-wavelength, liquid-crystal tunable filter (LCTF) and fitted to the front of the camera lens. Preferably, the power supply and a software program are used to power up and control the image acquisition hardware. Preferably, the apparatus is portable and the acquisition of data is performed in real-time or near real-time. Preferably the tissue examined can be the skin, such as that of the volar (inner) forearm. Two such lens, filter and detector subsystems, one for visible and the other for NIR wavelength collection can be combined and integrated into a single functioning system.

In another embodiment of the invention, an acousto-optic tunable filter (AOTF) is fitted between the lens and the camera or in front of the lens. Wavelength selection occurs by changing the frequency of the acoustical wave via computer controlled driver. Depending on the desired optical design, an additional lens can be used between the camera and AOTF.

In another embodiment of the invention, an infra-red thermometer is co-aligned with(in) the HSI system to measure the temperature of the ROI surface. The thermometer could be extended to an array of thermo-sensitive devices that provide a digital image of the temperature distribution on the observed surface. The latter is incorporated into HSI data analysis to determine onset and progression of shock.

Another embodiment of the invention is directed to a method for acquiring MHSI data from a patient comprising illuminating a region of interest on tissue of the patient, collecting data images of the region of interest with a detector, converting the data images to optical density units using an algorithm, creating a hypercube of the data images, and calculating any or all of the following: oxyhemoglobin, deoxyhemoglobin and water coefficients and using these calculations to derive any or all of the following physiologically relevant parameters: oxygen delivery, oxygen extraction, total hemoglobin, tissue hyperspectral oxygen saturation ($S_{HSI}O_2$), and hydration levels for each spectrum in the hypercube. Any or all of these parameters are used in order to derive a hyperspectral shock index.

From the collected data, calculations are performed to provide information as to the chemical composition of the ROI. Preferably any one or more of the following coefficients representative of the concentration of the substance present are calculated from the data: oxyhemoglobin, deoxyhemoglobin and water. More preferably oxyhemoglobin and deoxyhemoglobin and water coefficients are calculated for each pixel of the image or for representative pixels, groups of pixels, region of the ROI or the entire ROI. Most preferably, only oxyhemoglobin and deoxyhemoglobin coefficients are calculated.

One or more calculated coefficients are used by the system or by a diagnostic module of the system to derive information on physiology or physiologic state or physiologic derangement or pathophysiology. Preferably this reflects broader physiology than that of the specific piece of tissue imaged. More preferably this information reflects or is correlated with at least regional physiology. Most preferably this information reflects or is correlated with systemic physiology or metabolic state.

Algorithms have been developed by the system or by a diagnostic module of the system to reduce and present the information. Preferably these algorithms are designed to generate a scalar index value or scalar value that can be correlated to or associated with variations in the physiologic state under study. Preferably this is a shock index. Preferably, this index can be considered to be a vital sign and serve as a surrogate or non-invasive non-contact or remote method of obtaining a vital sign. It may or may not be designed to closely correlate with one of the currently standard vital signs such as heart rate or blood pressure. More preferably, a shock index will correlate with more advanced measures of hemodynamic status such as cardiac output, stroke volume or DO2. Most preferably, the shock index will be correlated with outcomes. Preferably the shock index will provide improved or earlier information about the patient status in advance of other metrics.

In other embodiments other indices can be derived by the system or by specific diagnostic modules for other states of disease or physiology. Examples of such indices include ones derived for diabetes, congestive heart failure, renal failure, fluid retention, dehydration, hypertension, hemorrhage, sepsis, pulmonary failure, hypoxia among others. These can similarly be correlated with current measures associated with the various physiological or pathologic states or with outcome data to provide an improved metric.

In an alternate embodiment, a set of numbers reflecting the coefficients themselves will be presented along with scales to permit interpretation. In yet another alternate embodiment, pertinent information is presented as a single or series of black and white or false color images reflecting both spatial and spectral tissue characteristics. Preferably the images will be reported in association with a scale to permit easy interpretation. In another embodiment a simple indicator of metabolic state is provided. Preferably, this is in the form of one or a series of lights that signal the operator as to the state of the patient. In another embodiment, verbal or written instructions are presented on a screen.

Images may be presented in any of a number of methods including on the MHSI imager itself, on a remote screen, by projector or via a heads-up-display.

Prespecified lighting is used or lighting is measured or estimated or recorded. Preferably the system is calibrated to take into account ambient lighting as well as any light administered by the instrument. Calibration steps determined to be necessary are identified either automatically or manually or by a combination of the two and steps taken to implement this calibration is undertaken either manually or automatically or as a combination of the two. Preferably calibration steps are used to assess and utilize or correct for ambient light.

In one preferred embodiment, a tunable light source, a tunable filter or both are used as spectral separators to provide specific spectral data for analysis. In another preferred embodiment, specific wavelength light sources, preferably LEDs are used to provide the data input and obviate the need for some or all of the spectral separators or filters.

Preferably lighting is provided for the device during all or part of the data collection process. More preferably the instrument provides prespecified lighting. Preferably, the instrument collects at least one set of data with only ambient lighting. This data set could be a single wavelength band collection or all or part of the entirety of the wavelength bands measured by the device. In another embodiment, ambient light is utilized as the light source and measured by the device for use in calibration. Preferably if the ambient light is insufficient, the operator will be notified. Most preferably, if the ambient light is insufficient it will be supplemented by lighting from the instrument either manually or automatically or as a combination of the two.

Other embodiments and advantages of the invention are set forth in part in the description, which follows, and in part, may be obvious from this description, or may be learned from the practice of the invention.

DESCRIPTION OF THE FIGURES

FIG. 15 Hyperspectral data collection through CBW mask. From top to bottom: 1) photograph reconstructed from hyperspectral images of region of interest; 2) Spectra obtained through mask lens demonstrating expected heterogeneity; and 3) unregistered "raw" spectral image with spatial variation which is advantageous in image processing algorithms. Note reflective glare does not hamper analysis.

DESCRIPTION OF THE INVENTION

Figure 1:
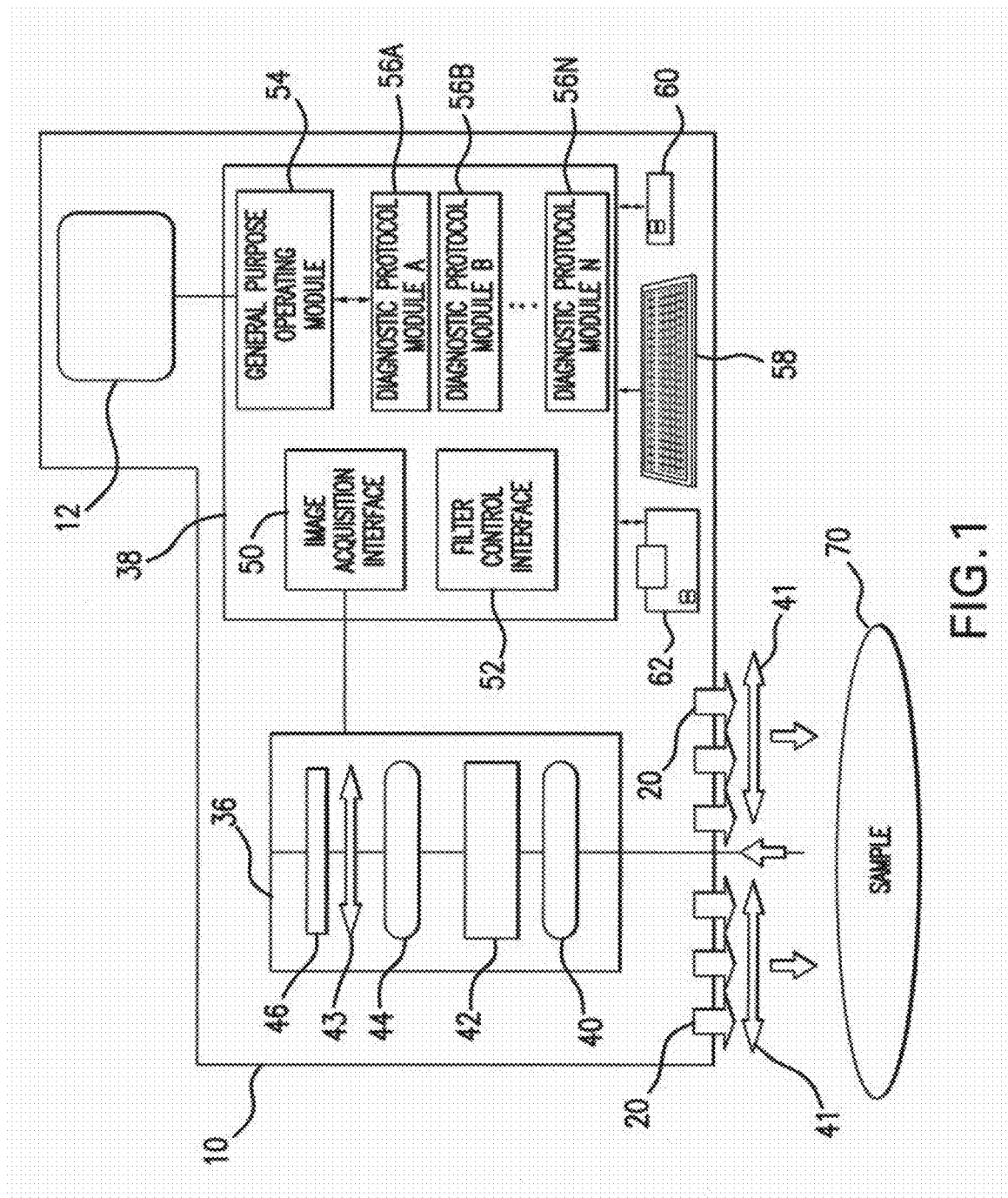
FIG. 1 HSI system with light separator.

Spectroscopy has been used to monitor metabolic status in a variety of tissues. For example, spectroscopic methods are incorporated in pulse oximeters, which utilize the different oxy- and deoxyhemoglobin absorption bands to estimate systemic arterial oxygen saturation. The measurement provided by pulse oximetry is, however, inadequate as a method to diagnose or monitor shock. While pulse oxymetry can provide a point measurement of arterial oxygen saturation, it does not provide a measure of total hemoglobin or of tissue oxygen extraction or of tissue hydration. In so doing, pulse oximeters only provide a portion of the information necessary to make an assessment of physiologic state associated with shock and hemodynamic condition. This is significant, as a drop in total hemoglobin or the mismatch between oxygen delivery and oxygen extraction or the pattern of the skin circulation carry important information and can be important warning signs. Pulse oximeter derived arterial oxygen saturation actually provides more information as to pulmonary as opposed to circulatory function, and arterial saturation can be preserved late into profound shock, especially if the patient is being ventilated with high concentrations of oxygen.

Another parameter important in determining adequacy of circulation and/or perfusion to the tissues is oxygen extraction by the tissues. By recording both oxyhemoglobin and deoxyhemoglobin information and using this to report information regarding both oxygen delivery and oxygen extraction (respectively), medical hyperspectral imaging (MHSI—which herein is understood by those skilled in the art to refer to either or both medical multispectral or hyperspectral imaging) reports on tissue metabolism and the adequacy of tissue perfusion to maintain tissue health and viability. Using both pieces of information, tissue OxyHb and DeoxyHb hemoglobin levels calculated from MHSI data can deliver information as to tissue oxygen saturation ($S_{HSI}O_2$) and total hemoglobin. Water levels calculated from MHSI data can deliver information as to the state of hydration of the tissue. In the shock state, the patterns of hyperspectral imaging also are useful to demonstrate the body's response to hemodynamic compromise. In the body's response to hypovolemia, in order to centralize blood flow, blood is often shunted away from the skin very early in the process. Thus, by monitoring the skin and the pattern of its microcirculation or its hydrational state, we obtain early information as to the severity of hemodynamic compromise. Microcirculatory changes related to other disease states such as diabetes, systemic infection or cardiac or pulmonary disease can be similarly evaluated. Other acute or chronic physiologic or metabolic changes can be identified, assessed or tracked by similar methods (Greenman et al., Lancet 2005; 366: 1711).

Changes in tissue images reflect both global changes, regional changes related to regional blood flow and hydration and more localized changes associated with the specific response of the microcirculatory bed under examination. Comparison of responses of different tissues or microcirculatory beds (for example, skin versus buccal mucosa, or skin from a peripheral site such as the forearm versus skin from a more central site such as the chest wall) and their relative change over time provides additional information.

In hospital settings, a number of measurements can be made in an attempt to monitor shock. Progression toward circulatory collapse is often monitored based on significant reductions in blood pressure and oxygen carrying capacity of the blood, and elevations in heart rate, and changes in pulse character. There are several compensatory mechanisms that buffer against changes in blood pressure and oxygen carrying capacity, limiting the use of these measurements for early assessment of shock. The appearance of hypotension and other signs and symptoms of shock do not mark the beginning of circulatory compromise, but rather represent the beginning of decompensation, i.e., a point in time when it may be too late to introduce effective therapy.

Another standard vital sign, heart rate, is a notoriously non-specific indicator of shock. Elevated pulse rate in a wounded soldier or injured patient may be impossible to accurately interpret since "fight-or-flight" responses are a natural consequence of battle. More invasive or extensive measurements are not practical during combat or to first or early responders in the more conventional ambulance or emergency room settings. In these settings, it is likely not possible to implement invasive monitoring such as, for example, pulmonary artery (Swan-Ganz) catheterization, which gives measurements of blood gases and cardiac output. Thus in both military and civilian arenas a need exists for small, noninvasive and portable measurement systems.

Non-invasive measurements of blood gases can be made using, for example, transcutaneous oxygen partial pressure and/or carbon dioxide partial pressure ($PtCO_2/CO_2$). One shortcoming of these measurements is that they rely on a small sample size which does not accurately reflect overall tissue condition. In addition, probe placement itself on the skin alters its blood flow and physiology.

MHSI data may also be combined with data provided by one or a combination of the following measurements: skin temperature, core temperature, heart rate, R-R interval variability, arterial blood pressure, end tidal CO2, tcPO2, cranial Doppler, pulse oximetry, laser Doppler, ultrasound, NIR point spectroscopy, nerve conduction, cardiac output, stroke volume, central venous pressure, pulmonary artery pressure, pulmonary capillary wedge pressure, tissue hydration measurement, blood chemistry values such as pH, lactate, to provide additional information to the care giver, improve diagnostic accuracy or deliver earlier warning of alteration in physiological status or impending shock.

Skin is a particularly good choice for monitoring. In addition to its easy availability to camera-based technology such as MHSI, there are well appreciated responses of the skin microcirculation to shock and to other systemic disease states. By monitoring the skin MHSI can track changes associated with a decrease in blood or red cell volume due to causes including blood loss, hemodilution, an increase in tissue water or shunting blood away from the skin to protect blood flow to central organs. Information is also obtained as to the response of the autonomic nervous system which has specific impact on the skin microcirculation and can provide additional information as to the cause and severity of the insult or disease state and of the body's response. This may be different in different disease states, in the different forms of shock or in the case of septic shock to specific organisms. Skin measurements taken with MHSI can be used to derive information about oxygen delivery, oxygen extraction, and hydration level which can secondarily be used to evaluate the physiology associated with a variety of disease states such as shock and diabetes.

Oxyhemoblobin (OxyHb), deoxyhemoglobin (DeoxyHb) and water coefficients can be presented independently as images or as scalars reflecting a mean value across a region of interest (ROI), or the oxyhemoblobin and deoxyhemoglobin coefficients can be used to calculate hyperspectral tissue oxygen saturation ($S_{HSI}O_2$=OxyHb/(OxyHb+DeoxyHb)), total hemoglobin. This information can be presented as black and white or false color images, or oxyhemoglobin and deoxyhemoglobin values (or their combination equivalent to oxygen extraction and delivery) can be presented together in a format such as a blood pressure (e.g. XX/YY). This presentation can be used to represent oxyhemoglobin and deoxyhemoglobin values for any pixel in the ROI, to present the average oxyhemoglobin and deoxyhemoglobin values over the entire ROI or over any subsection of the ROI or the oxyhemoglobin and deoxyhemoglobin values can be combined by a formula or an algorithm to a single number (e.g. hyperspectral shock index). At any of these stages, additional data from the water coefficient or other physiological or biochemical values can be added to enhance the utility of the technique. For example a different color scheme could be chosen to present OxyHb, DeoxyHb and water coefficients in a given image, or the scalar value for each coefficient for a pixel or a region could be presented as XX//YY//ZZ.

For example, the mean of the OxyHb coefficient determined from skin at a region of interest decreased preceding the onset of shock while the standard deviation of this value increased. These trends were observed in both the human LBNP in pig hemorrhage experiments. In addition, the hyperspectral shock index, which is derived from the mean and standard deviation of the OxyHb coefficient, the blobbiness index and the temporal index, was shown to be correlated to the heart rate and lower body negative pressure, and reasonably correlated with stroke volume and pulse pressure. Using diabetes as an example, the OxyHb/DeoxyHb values are typically around 30/40 for control subjects and 20/50 for subjects with diabetic neuropathy.

Anesthesia may alter control mechanisms for cutaneous blood flow, causing a dampening of the blood flow oscillations which normally occur in response to hypovolemia. Hyperspectral images may be different in anesthetized versus awake patients, may vary with depth of anesthesia, or may vary with particular medications administered. A library of responses under various pharmacologic situations could be used to improve results. For example, U.S. Pat. No. 6,640,130 by Freeman et al., teaches the use of extracting information from the plurality of images and spectra including thermal measurements by way of multivariate classification algorithms. Addition of information relative to patient condition, other hemodynamic or other parameters, presumptive diagnosis or therapies administered could improve results. Braverman and colleagues described the relationship between the microanatomy of the cutaneous circulation and regional heterogeneity in blood flow by laser Doppler flowmetry. They also described synchronicity in cutaneous bloodflow oscillations between sites on ipsilateral and contralateral limbs, suggesting that such oscillations are controlled centrally by the sympathetic nervous system.

Further studies employing MHSI in unanesthetized humans undergoing lower body negative pressure demonstrated that an increase in regional heterogeneity in the region of interest (ROI) of images can be demonstrated by the hyperspectral measurement of tissue oxyhemoglobin and oxygen saturation ($S_{HSI}O_2$) and that changes in this heterogeneity of the oxyhemoglobin and $S_{HSI}O_2$ is a prominent feature of the response to central hypovolemia, as is a greater change in heterogeneity between images collected at different time points.

Thermoregulation is a major function of the cutaneous circulation, and hypothermia is commonly present in trauma casualties. Treatment is also now under development to assist in the early care of patients with hemodynamic insufficiency and other medical problems. The relationship between systemic hypothermia and localized cutaneous total hemoglobin, oxygen delivery, oxygen extraction and oxygen saturation can be defined by MHSI technology. The decrease in mean cutaneous oxygen saturation ($S_{HSI}O_2$) and OxyHb values during the hemorrhagic shock study were not caused by systemic hypothermia. Core and skin temperature were maintained.

In a separate pilot study, moderate hypothermia (down to 32 degrees Celsius) did not produce the same mean changes in tissue oxygenation across the ROI that were observed with hemorrhagic shock. More significant changes were seen with deeper hypothermia (26 degrees Celsius). Possibly, decreased metabolic demands defended against desaturation during hypothermia. These experiments were done in anesthetized pigs and there may be far different results in awake or anesthetized humans. Different parameters and patterns are derived under these circumstances which will be useful in monitoring physiologic status under circumstances where hypothermia occurs or is induced. MHSI is useful in monitoring the systemic physiology and metabolic state associated with hypothermia.

Classically, physicians have used capillary refill as an indication of systemic perfusion. Several other patents describe methods that also attempt to give early detection of shock. Shani et al. (U.S. Patent Application Publication No. 20040249290) describe a shock monitoring device which consists of an optical device that registers changes in a patient's skin. In that patent, like the physician pressing the skin, pressure is briefly exerted on the patient's skin in a periphery. The time required for the skin to change from white to back to a pink color is automatically detected by the device, giving a measure of capillary refilling time.

As described above, blood pressure measurements are most commonly used to identify shock-related hypotension. Several recent patents have described additional ways of using blood pressure measurements to monitor shock. Sharrock et al (U.S. Patent Application Publication No. 20030040675) describe a non-invasive method for monitoring the cardiovascular system. In that approach, a pressure sensor is placed underneath a blood pressure cuff. "Suprasystolic" measurements are made, i.e. pressure measurements made when the cuff pressure is greater than the patient's systolic blood pressure. The time series recorded show an initial impulse generated by the heart beat, followed by a series of reflections from within the circulatory system. The patent describes a method for estimating the degree of vasoconstriction from the pressure time series. Data are presented showing that the suprasystolic measurements can aid in diagnosis of shock.

A second use of blood pressure measurements is described by Cohen et al. (U.S. Patent Application Publication No. 2004015816). In that method, a quantity proportional to cardiac output can be calculated from a blood pressure measurement by estimating an overall mechanical resistance for the circulatory tree. Cardiac output is clearly an important parameter in identifying the onset of shock, as described above. However, because the device estimates a quantity proportional to cardiac output (rather than cardiac output directly) the device would presumably require a baseline measurement for each patient before it could be used to detect the onset of shock. Additionally, the numerical value generated by a cardiac output measurement per se is not always associated with irreversible hemodynamic derangement, i.e. there is variability in the response or resilience of a given individual—this is more easily quantified and monitored with the multiple parameters available with MHSI.

Similarly, in more chronic conditions as diabetes or congestive heart failure, microcirculatory alterations and variations in oxygen delivery and extraction can be monitored and can provide useful information as to disease state or progression of disease. Also, data related to shock in a given individual may be related to a given baseline which reflects diabetes, congestive heart failure or other disease states that influence the microcirculation or the skin. With the increasing incidence of diabetes, an understanding of the manifestations of acute shock on a baseline of chronic diabetes is imperative. Similarly, congestive heart failure is a chronic condition, but one in which the evaluation of cardiogenic, hemorrhagic, septic or other shock could be particularly crucial. Again, with a baseline library of congestive heart failure parameters, the importance of features seen in such patients in shock is more easily interpretable. The approach is based on hyperspectral imaging applications, described in an earlier patent application by Freeman et al., U.S. Patent Publication No. 20040236229, which is herein incorporated by reference in its entirety.

One comment about the approaches described above is that they may in many cases be complementary to MHSI measurements. For example, estimates derived from blood pressure may give information about the overall circulatory system, while MHSI measurements provide a high-resolution image showing local changes of circulatory patterns in the skin.

MHSI is a method of "imaging spectroscopy." Spectroscopy is widely used to monitor metabolic status in a variety of tissues. For example, spectroscopic methods are incorporated in the pulse oximeters described above, which utilize the different oxy- and deoxyhemoglobin absorption bands to estimate arterial oxygen saturation. Point spectroscopy in the near-infrared range interrogates tissue hydration along with the tissue saturation of oxygen in subcutaneous tissue, muscle, and/or brain, and has been used for patient monitoring in hemorrhagic shock, in extremity compartment syndrome, and following head trauma.

Near-infrared measurements have been used to give a measure of blood oxygenation that potentially can be used in detecting shock. A recent patent publication by Ward et al. (U.S. Patent Application Publication No. 20040039269), describes a method of shock monitoring that uses ultraviolet, near-ultraviolet and near infrared resonance Raman spectroscopy and fluorescence spectroscopy for tissue interrogation. The present invention teaches, among other things, the use of visible and NIR diffuse reflectance spectroscopy for the detection of shock that does not require sensitive detectors required for collecting weak fluorescence and resonance Raman signals as described in Ward et al.

In regard to near-infrared (NIR) and related point spectroscopic measurements, these spectroscopic approaches do not result in images, and therefore do not deliver any information as to spatial distribution of blood flow or microcirculatory changes which are important in predicting the body's response to shock. Further, the hemoglobin absorption signal is much stronger in the visible range compared to the NIR. Given ever-present biological and optical noise, it is easier to quantify the hemoglobin-related processes in the visible range (as is done in the proposed MHSI approach) due to the higher signal-to-noise ratio. NIR spectroscopy has been primarily developed to monitor deeper tissues such as muscle and brain. While skin and subcutaneous measurements can be collected and have been reported, because of the interoptrode distances and other technical issues, (perhaps including those related to skin heterogeneity) these results have been variable, such that these techniques have yet not become widely used in clinical practice.

Used for decades in airborne systems for the analysis of geological features, HSI has recently been applied to biomedicine. The spectrum of reflected light is acquired for each pixel in a region, and each such spectrum is subjected to standard spectral analysis. This allows the creation of an image based on the chemical content of the region of interest (ROI). It has been employed in microscopic studies of histologic sections. In vivo, MHSI has been used locally to demonstrate the macroscopic distribution of skin oxygen saturation in models of ischemia-reperfusion, following nitric oxide inhalation and inhibition, and in patients with sickle cell disease. One application of MHSI has been in the early prediction of tissue viability following plastic surgery: tissue that has insufficient oxygenation to remain viable is readily apparent from oxygen saturation maps calculated from near-infrared spectral images acquired immediately following surgery. By contrast, clinical signs of impending necrosis do not become apparent to the naked eye for 6 to 12 hours after surgery. Assessment of tissue viability following burns has also been performed.

MHSI information about the microcirculation has been useful in the evaluation of regional and systemic microcirculatory changes in people with diabetes and correlations have been found between MHSI data reflecting regional (e.g. foot dorsum) and systemic (e.g. forearm) tissue oxygenation and $S_{HSI}O_2$ and diabetic foot disease and the risk of developing ulceration. Typical values for $S_{HSI}O_2$ are 42%, 32% and 28% in control subjects, diabetic subjects and diabetic subjects with neuropathy, respectively, (Greenman et al. Lancet 2005; 366: 1711). Subjects with neuropathy have a higher risk for developing foot ulcers. Nerve function is important in controlling microcirculation as evident by the lack of vasodilation in neuropathic diabetics that is commonly seen adjacent to injured skin in otherwise healthy individuals.

Described herein is the application of MHSI to the assessment of systemic disease to meet the substantial need for apparatus and methods for performing real time or near real time assessment and monitoring of shock in both military and civilian arenas at an in-depth level that hyperspectral imaging provides.

As embodied and broadly described herein, the present invention is directed to methods and apparatuses for assessing an array of physiologic parameters including the delivery and extraction of oxygen and water delivery to tissue (including skin, and the mucosa or serosa of various organs) and local tissue response to the adequacy of this delivery by hyperspectral or multispectral imaging in real time or near real time.

The invention described herein uses hyperspectral or multispectral imaging as a noninvasive and generally although not necessarily, noncontact means of monitoring changes in tissue and the microcirculation (here described for obtaining images from the skin, but is not limited to the skin) that are indicative of systemic physiology including the state preceding shock or occurring during shock (whether hemorrhagic, hypovolemic, cardiogenic, neurogenic, septic or other shock states). Changes in microcirculation can also be indicative of other physiological states or derangements as described herein. and as a means for providing indicators for monitoring therapy or the adequacy of resuscitation and patient survivability. Unlike conventional methods, the MHSI approach employs an imaging system, and is capable of displaying and drawing attention to changes in the circulatory patterns in the skin and the changes in these changes. One specific type of change, mottling, is known to be a symptom of shock.

The invention is applicable in military, critical care and chronic disease management arenas where there are microcirculatory or tissue oxygenation changes associated with shock, diabetes, infection, sepsis, dehydration, hypothermia, hypoxia, low gravity environments, congestive heart failure, hypertension, hypotension or other physiologic derangement, when the assessment of physiologic state or of the response or potential response to therapy is advantageous. Shock represents one end of the spectrum as an example of acute microcirculatory pathology. Diabetes represents the other end of the spectrum, and is associated with slower, more chronic changes which, however, are also reflected in microcirculatory changes.

The instruments and methods of the invention may also be applied to many forms of shock and other acute and chronic conditions in which physiologic monitoring for screening, assessment, diagnosis, early warning, monitoring of therapy or assessment of survivability is useful. In addition to or instead of the microcirculatory changes associated with local response to the mismatch of oxygen delivery and oxygen extraction and changes in hydration that we can observe with hemorrhagic shock, we anticipate other specific findings associated with other forms of shock which can also be identified, assessed and quantitated by hyperspectral imaging. For example, in septic shock, the presence of a variety of inflammatory mediators influences the microcirculation. These microcirculatory changes are in turn identified and monitored using our MHSI techniques. This allows specific information as to the onset or progression of infection or shock or the monitoring of the efficacy of antibiotics, intravenous fluid administration, pressor agents to treat hypotension or acute cardiac decompensation (such as dopamine or neosynepherine), or other forms of therapy. The observed microcirculatory changes are also useful in determining the causative organism(s), which can be associated with idiosyncratic tissue signatures.

In other chronic conditions MHSI can be used to derive spatial and spectral data from the tissues to provide information relating to indications for administration of particular therapies and for monitoring such therapies. This includes use of MHSI measurements to assist the physician in treating patients with conditions such as hypertension or congestive heart failure and provide useful information which can assist in decisions relative to the use of specific antihypertensive or after load reducing agents. Here, patients can be selected for specific therapeutic regimens or therapies can be monitored with MHSI. Additional uses include monitoring native tissue or wounded tissue in the face of steroid therapy. Another use includes monitoring for systemic effects of neurological defects.

Another iteration is an advanced metabolic monitor for ICU and critical care purposes to define adequacy of metabolic support and tissue oxygen delivery and extraction. This is especially useful to determine combined adequacy of ventilatory and circulatory support to optimize care and adjust therapy. Another use is to assess adequacy of ventilation. In patients with damaged lungs, sometimes over ventilation or over oxygenation can contribute to tissue damage and prolong hospital stay or even lead to poor long term outcome or death and it would be useful to determine the minimum amount of ventilator support truly required to maintain adequate tissue oxygenation and ventilation. This can be determined by monitoring the levels of oxygen delivery and oxygen extraction as derived from measurements of tissue oxyhemoglobin, tissue deoxyhemoglobin, and/or by using information provided by both of these measurements, with or without the addition of information as to the water content of monitored tissue (e.g. skin, mucous membrane or other tissue). This is also useful in determining the need for pulmonary drugs including bronchodilators, surfactants, etc.

Hyperspectral imaging of patients exposed to biological or chemical agents permits simple implementation by non-professional staff for rapid use in the field, clinic and hospital settings without the necessity for prior patient preparation or subsequent lab work. In one embodiment, using spectral and spatial data of biologically relevant compounds, MHSI is used to identify physiologic changes to evaluate infection of individuals or populations either in association with sporadic infection or in an epidemic. In these settings MHSI provides a useful tool for triage, screening, diagnosis, determining therapy, monitoring of therapy, monitoring disease progression or resolution. In relation to possible exposure to chemical and biological warfare (CBW) agents, MHSI determines the likely pathogen/class responsible and evaluates the extent of exposure, progression of disease and effectiveness of treatment. A rapid, low-cost, non-invasive screening tool that differentiates between pathogen classes permits assessment of key portions of the population during an epidemic.

Locally, MHSI can evaluate the "take" of a variety of immunizations such as smallpox using a combination of oxyhemoglobin and deoxyhemoglobin and water data images to facilitate diagnosis. At some level, all pathogens lead to microcirculatory changes and the body itself acts as a "bio-amplifier" in that it mounts immune responses that include localized or disseminated cutaneous manifestations. The response itself can be interrogated to detect subtle changes that indicate exposure to a bioagent. A characteristic effect of the bioagent on the organism as a whole can be relatively dramatic and produce a larger "signal" for detection, in contrast to the more difficult task of identifying a few small bacteria or virus particles in situ. Through leveraging this natural response, in one embodiment, MHSI is useful as a screening tool to evaluate those at risk of infection in a natural epidemic or biowarfare scenario.

Beyond the CBW applications, hyperspectral technology more widely offers the capability for relating local information to systemic pathophysiology in the setting of infection. Rapid and accurate determination and classification of infection would benefit a wide group of patients ranging from patients immuno-compromised due to HIV or chemotherapy to elderly or very young patients presenting in septic shock. By distinguishing between classes of infectious organisms, MHSI can assist in determining the initial choice of antibiotic regimens or assist in the diagnosis between viral gastroenteritis and appendicitis. In another iteration, MHSI is designed to assess less profound metabolic alterations and the sequelae of chronic diseases such as diabetes. Diabetic patients are at high risk for limb loss secondary to atherosclerotic peripheral vascular disease or diabetic foot ulceration and would benefit greatly from a device which could detect spreading or systemic sequelae of infection at an early stage.

In the face of a chemical or biological exposure, MHSI can be used to rapidly and accurately assess the hemodynamic status of wounded or affected individuals. Local changes in either OxyHb and DeoxyHb and $H_2O$ or any combination of these parameters can be used to assess the physiologic state of a victim potentially exposed to a chemical or biological agent. Given specific changes related to an immune or inflammatory, cardiovascular or neurological or other response, severity of exposure, identification of agent, duration of exposure, severity of response and other parameters useful to the care giver can be assessed and followed over time. MHSI can provide a non-contact means of obtaining a useful "vital sign" to assess patient condition without the need to touch the patient or remove any protective gear. Cumbersome chemical biowarfare (CBW) personal protective gear may prevent medical personnel or first responders from the access required for standard assessment of casualties who may also be wearing CBW gear. Taking a pulse or measuring blood pressure is often impossible. Any device placed in contact with a potentially contaminated individual may also be contaminated and may not be able to be reused without onerous cleansing measures or disposable covers. Therefore, use of MHSI as a remote sensing technology to provide physiologic and hemodynamic assessment in such circumstances is highly advantageous. Also, preferred is a sensing technology that will see through portions of the CBW gear such as clear plastic faceplates or other such windows in the gear, or directly through opaque fabrics and other such materials.

In one embodiment, the proposed invention could provide trauma triage by providing a "vital sign" reporting critical casualty information to the battlefield medic encumbered by chem/bio protective clothing. A resulting MHSI algorithm for delivering information which could be interpreted as a novel "vital sign" measurement would inherently identify the measures required in order to provide the most effective casualty care and remote triage. This invention also provides the medic with a greater decision making capability for prioritizing casualty care based on otherwise unavailable information about live/dead status, severity and progression of the injury and which injuries require life saving interventions.

In one embodiment, a personal digital assistant (PDA)-like device carried by the battlefield medic might have a single button that could be pushed even with protective gloves on to take a HSI image and provide a numerical read out or even more simply, a simple visual code (green, yellow, red) of a downed soldier's medical status. MHSI could reduce combat mortalities by enabling combat medics in CBW gear to: 1) commence triage within moments after a soldier is wounded; 2) receive more accurate information of wound severity and progression to shock; and 3) optimize available treatment and evacuation. Finally, since the killed-in-action rate for battlefield medics (even absent CBW concerns) has been as high as double that of infantryman, HSI could be instrumental in reducing risk to the combat medic by providing early identification of dead or unsalvageable soldiers and particularly in the chem/bio arena by permitting non-contact and more remote measurements.

In one preferred embodiment, MHSI is used to provide a hand-held, robust, turnkey system for near-real time information based on a combination of spatial and spectral data. Designed for use as a stand-off tool, this embodiment requires minimal operator dexterity and the device is operable by an end-user in CBW attire. Optimally, a battlefield or CBW agent detection device would provide information from a great distance with a remote or local light source, but at the very least, an operating distance of even inches would provide significant advantage over an assessment requiring individual contact. Monitoring of an exposed hand or the eye/cheek region through a standard gas mask could provide the surface necessary for physiologic evaluation. Hyperspectral imaging can be used as a stand-off device as a non-contact vital sign monitor (e.g., non-contact diagnostic or vital sign) for use by a provider wearing CBW protective clothing to predict metabolic embarrassment and impending hemodynamic collapse and at various distances and in cases where access to the victim is difficult CBW protective clothing.

In one preferred embodiment, MHSI provides localized spatial and spectral data as described that is used in judging the vasodilatation accompanying anesthesia and the potential use of vasoconstrictive agents such as neosynepherine to offset effects of either general anesthesia or regional (e.g. spinal) anesthesia on systemic or lower body vasculature.

In another preferred embodiment, a portion of the proposed invention is attached by a nonconstricting arm band or other fixation device to the body for stabilization and to facilitate multiple readings over time. Image data or calculated results can be sent by wire or electronically to a distant monitor. Another embodiment could provide a method of fixing the imager near or lightly touching the tissue to obtain image data from skin or from oral, rectal or bladder mucosa or other tissue.

In one embodiment, preferably with a specific diagnostic protocol, the proposed invention can assess the adequacy of pulmonary and circulatory function following a pulmonary embolus.

In another embodiment, preferably with a specific diagnostic protocol, the proposed invention can assist in the evaluation and management of chronic anemia, leukemia or other cancers in assisting the determination of the adequacy of a low hematocrit to meet the metabolic requirement of end organ tissue (such as skin).

In another embodiment, preferably with a specific diagnostic protocol, the proposed invention can assist in the evaluation and management of chemotherapeutic agents and the side effects thereof.

In another embodiment, preferably with a specific diagnostic protocol, the proposed invention can assist in the management or evaluation of systemic manifestations of organ rejection following cardiac or renal transplant.

Given the unique spectral signature of carbon monoxide, in one embodiment, MHSI is designed to assess and report carbon monoxide levels for use in diagnosing and monitoring patients following potential or real carbon monoxide exposure and to assist in the determination of tissue levels of carbon monoxide and in monitoring and adjusting therapy.

One embodiment of the proposed invention is tailored for use in the screening, diagnosing, evaluating and monitoring of trauma or burned patients who have either circulatory or ventilatory compromise or both.

One embodiment of the proposed invention is tailored for use monitoring patients with fevers or infections. Given the inflammatory and vasoactive responses with microcirculatory consequences, MHSI is used to monitor the ordinary response to a variety of organisms or the response of patients that are immunosuppressed with chemotherapy or intrinsic disease (e.g. AIDS).

One embodiment of the proposed invention is tailored for use to identify the need for transfusion and when the red cell volume or blood volume has been replaced adequately.

Because of its capability of measuring hemoglobin and hemoglobin breakdown products, the proposed invention is useful for evaluating new blood substitute products and for monitoring their use in the clinical setting. This could range from determining adequacy of oxygen carrying capacity in the circulating blood to following with MHSI's spectral and spatial features, the potential extravasation of the substitute from the capillaries or small vessels.

One embodiment of the proposed invention is tailored for use in the determination of whether to give volume and what kind (e.g. blood or crystaloid) versus pressor agents such as epinephrine to a hypotensive patient.

One embodiment of the proposed invention is tailored to select antihypertensive therapy in cases of acute or chronic hypertension and monitoring efficacy.

One embodiment of the proposed invention is tailored for drug development or in the selection or assessment of patients for clinical trials as a research tool or patient selection and monitoring of any drug or drug candidate that has an influence on tissue microcirculation or hydration.

While we have primarily focused on readings from skin, similar instrumentation (with different front end optics and data pre-processing specific to the tissue and site under evaluation) are used and data analysis could be performed from data obtained from other sites such as buccal, bladder, rectal, esophageal, nasopharyngeal or other mucosa, nail bed, ear lobe, palmar or plantar skin, or the serosal surface of internal organs. Imaging systems and probes to obtain appropriate images could be specifically designed for each location. These measurements could be taken either at intervals or continuously and recorded for static measurements or for trending information.

By revealing changes in tissue hydration, total hemoglobin, oxygen delivery, oxygen extraction, $S_{HSI}O_2$ or circulatory patterns that correlate with adverse outcomes, the MHSI approach is additionally able to provide information about patient survivability, shock state, physiology, hydration status, capability to compensate for volume loss, type of shock, organism or class of organism responsible in infection or septic shock, and efficacy or adequacy of therapy. Water content in the tissue is also useful in this determination and is incorporated with total hemoglobin, oxygen delivery, oxygen extraction, $S_{HSI}O_2$ or circulatory pattern or temporal shift data or used independently to deliver early information relative to shock or an index which can be correlated with other useful hemodynamic parameters. Data and algorithms can be built around each of following three types of data: 1) just visible MHSI with a) oxy and spatial information or b) oxy and deoxy and spatial info or c) $S_{HSI}O_2$ with spatial info can be used, d) mean change with oxy, e) mean change with $S_{HSI}O_2$, 2) just infrared MHSI data with mostly water and some deoxy information as mean across ROI, and 3) any combination of 1 with 2

In general terms, the invention uses an imaging system to acquire a multi-dimensional "hypercube" of data describing a region of the skin or other tissue. This could be composed of many wavelength bands or at least 2 bands that help to provide spectral information across the ROI. The hypercube contains information about optical absorbance as a function of spatial dimensions, wavelength, and time. These data can be processed to yield an estimate of the abundance of chemical species as a function of spatial location and time. For the purposes of shock monitoring, images of the abundance of blood oxyhemoglobin and deoxyhemoglobin are particularly useful. These abundance images can be used to estimate tissue blood volume.

In healthy young individuals and in experimental animals, in the absence of shock, skin oxygenation appears relatively homogeneous across a given ROI. During various types of shock, several types of response can occur, either separately or concurrently, of these, four are described in more detail herein. First, shifts in the range and overall levels of quantities such as OxyHb, DeoxyHb and water in the tissue can be seen. Second, mottling of the skin may be observed. Mottling is a result of vasoconstriction which causes the OxyHb and DeoxyHb levels to become uneven across the skin. Regions of relatively higher and lower tissue oxygenation are seen, giving a mottled appearance. Third, the location of these regions can shift over time in response to changing constriction of the vasculature (temporal shift). Fourth, there is the appearance of new circulatory patterns in response to shock, some of which appear to be correlated with poor outcomes. In older and diabetic patients, there is a greater degree of baseline heterogeneity and a lower mean level of OxyHb and $S_{HSI}O_2$.

The present invention exploits the responses described in the last paragraph by using image processing techniques to generate a series of metrics. These metrics, described herein, include the average and the spread of levels in an image, measures of mottling, and measures of how rapidly the skin changes over time. These metrics are either used separately or combined together to derive an index that gives an early indicator of shock. Image processing methods are used to highlight circulatory features that are believed to be indicative of patient survivability. The HSI system uses an image processing technique to display gradients present within the ROI based on derived profiles of chemical concentrations. Derived scalar values that correlate with a given physiological state can also be presented.

First, the method used for acquiring HSI data, registering the images, and estimating relative abundances of chromophore is described. Second, algorithms for processing the images to detect overall, large-scale changes in the hyperspectrally derived quantities are derived. Third, image processing algorithms for detecting and evaluating local heterogeneity in the skin are derived including spread within the variable-size ROI. Fourth, mottling and patterned features of the skin are derived. Fifth, changes in mottling patterns over time are derived. Finally, methods for detecting features in the image that may indicate likely patient outcomes or the severity of the shock response or physiological derangement are described.

Accordingly, one embodiment of an appropriate HSI apparatus is described before the five processing steps.

Medical Hyperspectral Imaging System

In one embodiment, HSI data is presented in a very intuitive form by pairing a HSI pseudo-color image with a high quality color picture composed from the same HSI data. The identification and assessment of the region of interest (ROI) is easily achieved by flipping between color and HSI images or merging these images, and can be enhanced by zooming in on the ROI for enhanced resolution and additional information. The images can be seen on a computer screen, projector or heads-up-display, and/or stored and transported as any other digital information, and/or printed out. The presented image reflects the high resolution of the hyperspectral imager and can be improved with upgraded hardware. Alternatively, the data can be presented as single scalar numerical values for the entire ROI, any given pixel or selected region within the ROI. In this embodiment, preferably, oxygen delivery and oxygen extraction data can be presented in the form of XX/YY. Similar to a blood pressure and easy to understand, such a measurement carries both oxyhemoglobin and deoxyhemoglobin information but gives a more complete picture than a single scalar variable, since each of the two components carries specific information. If water is also presented it can be presented as XX/YY/ZZ.

Due to the complexity of the biological system, medical personnel want to have as much information as possible about a given case in order to make the most-reliable diagnosis, but need it to be reduced to a form amenable for facilitating decision making. MHSI provides additional information to the doctor that is not currently available and can be used along with other clinical assessments to make this decision. MHSI provides images for further analysis by the human; initially results can be compared to a lookup table. Ultimately, a computer algorithm can be used that automatically matches the results to the outcome expected from the lookup table.

Additionally, HSI transcribes vast multispectral or hyperspectral information into one image which presents complex data via millions of color shades which represent fine gradations in a gradient map. The particular color and distinct shape of features in the pseudo-color image allow discrimination between tissue types such as tumor, connective tissue, muscle, extravasated blood, and blood vessels. MHSI also allows the near-real time differentiation of tumor grade that will be useful in making appropriate medical decisions.

The main purpose of MHSI is the collection and presentation of physiologically relevant data in an easily interpretable numerical, image or other format in order to: 1) expand human eye capabilities beyond the ordinary; 2) expand the human brain capabilities by pre-analyzing the spectral characteristics of the observable ROI; and 3) perform these tasks with real or near-real time data acquisition. The aim of the algorithm is to assist the human to diagnose and assess the condition of the observable subject.

MHSI is successful because it carries more information than visual imagery, using the spectral data of reflected electromagnetic radiation (ultraviolet—UV, visible, near infrared—NIR, and infrared—IR), and since different types of tissue reflect, absorb, and scatter light differently, the hyperspectral cubes contain enough information to differentiate between tissue conditions. Here local tissue conditions are used to collect data that is relevant to the systemic condition or physiology of the individual or organism. MHSI is robust since it is based on a few general properties of the spectral profiles (e.g. slope, offset, OxyHb, DeoxyHb, and water); therefore it is relatively flexible with respect to spectral coverage and is not sensitive to a particular light wavelength. MHSI is fast, because it uses fast image processing techniques that allow superposition of absorbance, scattering (derived from slope and offset), and oxygenation information in one pseudo-color image.

An image cube can generally be collected in under a minute, but typically in a short period of time. The simplicity of image processing techniques allow for the display of results in real-to-near-real time. MHSI is easily interpretable since it can deliver an image where color differences reflect a gradient map of the concentration of different substances that reflect different tissue types, metabolism, physiologic state or condition. The distinction is graded and not binary. In addition, the color and the shape of structures depict different composition, physiology or metabolism or the level of viability of the tissue in the ROI.

A portable MHSI apparatus according to an embodiment of the invention is depicted in FIG. 1. Portable apparatus 10 weighs less than 100 pounds, preferably less than 25 pounds, and more preferably less than 10 pounds. Preferably, the portable apparatus may be battery operated or more preferably, may have a connector adapted to connect to an existing power source.

Portable apparatus 10 comprises an optical acquisition system 36 and a diagnostic processor 38. Optical acquisition system 36 comprises means to acquire broadband data, visible data, ultraviolet data, infra-red data, hyperspectral data, or any combination thereof. In a preferred embodiment, optical acquiring means comprises a first-stage imaging optic 40, a spectral separator 42, a second-stage optic 44, and an imaging sensor 46. There may be one or more subsystem 36s present, for example a single subsystem 36 could be built around either a visible or NIR LCTF. Alternatively, there may be one subsystem 36 built around a visible LCTF and one around a NIR LCTF. There may be one subsystem 36 which has an LCTF which accommodates both visible and NIR wavelengths or there may be one subsystem. Alternatively, optical acquiring means may be any acquisition system suited for acquiring broadband data, visible data, ultraviolet data, infra-red data, hyperspectral data, or any combination thereof. Preferably, one or more polarizers 41, 43 are included in the acquisition system to compile the light into a plane of polarization before entering the imaging sensor.

If the spectral separator 42 does not internally polarize the light, the first polarizer 43 is placed anywhere in the optical path, preferably in front of the receiving camera 46. The second polarizer 41 is placed in front of illuminating lights (20) such that the incident light polarization is controlled. The incident light is cross-polarized with the light recorded by the camera 46 to reduce specular reflection, or polarized at an angle to vary intensity of the reflected light recorded by the camera.

Illumination is provided by the remote light(s) 20, preferably positioned around the light receiving opening of the system. The light can be a circular array(s) of focused LED lights that emit light at the particular wavelengths (or ranges) that are used in the processing algorithm, or in the ranges of wavelengths (e.g., visible and/or near-infrared). The circular or substantially circular arrangement of the light sources in one or many circles surrounding the light receiving opening provides even illumination that reduces shadowing. The light wavelength selectivity reduces the total radiation onto the skin, and therefore reduces the effect of the observation on the observing subject. Particularly in the infrared regions, this can lead to less of a thermal effect on the skin and maintain the tissue in a more normal condition.

Although the preferred embodiment describes the system as portable, a non-portable system may also be utilized. Preferably, an optical head is mounted to the wall of the examination room. In another embodiment, the system has a portable table with an observational window overlooking the operating site.

The first-stage optic receives light collected from a tissue sample through a polarizer and focuses the light onto the surface of the spectral separator. Preferably, the spectral separator is a liquid crystal tunable filter (LCTF). The LCTF 42 is a programmable filter that sequentially provides light from selected wavelength bands with small (for example, 7-10 nm) bandwidth from the light collected from the sample. The second-stage optic 44 receives the narrow band of light passing through the spectral separator and focuses the light onto the image sensor 46. The image sensor is preferably, although not necessarily, a two-dimensional array sensor, such as a charge-coupled device array (CCD) or complementary metal oxide semiconductor (CMOS) detector, which delivers an image signal to the diagnostic processor 38.

The diagnostic processor 38 includes an image acquisition interface 50, that has an input responsive to an output of the image sensor 46 and an output provided to a general-purpose operating module 54. The general-purpose operating module includes routines that perform image processing, and that operate and control the various parts of the system. The general-purpose operating module also controls the light source(s) (e.g. LED array) allowing for switching on and off during measurement as required by the algorithm. The general-purpose operating module has control output provided to a filter control interface 52, which in turn has an output provided to the spectral separator 42. The general-purpose operating module also interacts with one or a number of diagnostic protocol modules 56A, 56B, . . . 54N, and has an output provided to a video display. The diagnostic process includes special purpose hardware, general-purpose hardware with special-purpose software, or a combination of the two. The diagnostic processor also includes an input device 58, which is operatively connected to the general-purpose operating module. A storage device 60 and printer 62 also are operatively connected to the general-purpose operating module.

In operation, a portable or semi-portable apparatus is employed near a target, e.g., volar forearm or other general area of interest. An operator begins by selecting a diagnostic protocol module using the input device. Each diagnostic protocol module is adapted to detect particular tissue characteristics of the target. In an alternative embodiment, the apparatus may contain only one diagnostic module adapted for general medical diagnosis.

Diagnostic processor 38 responds to the operator's input by obtaining a series of transfer functions and an image processing protocol and an image processing protocol from the selected diagnostic protocol module 56. The diagnostic processor provides the filtering transfer functions to the spectral separator 42 via its filter control interface 52 and then instructs the image acquisition interface 50 to acquire and store the resulting filtered image from the image sensor 46. The general-purpose operating module 54 repeats these filtering and acquiring steps one or more times, depending on the number of filter transfer functions stored in the selected diagnostic protocol module. The filtering transfer functions can represent band pass, multiple band pass, or other filter characteristics and can include wavelengths in preferably the UV, preferably the visible, preferably the NIR and preferably, the IR electromagnetic spectrum.

In a preferred embodiment, the light source delivering light to the ROI can be filtered, selected or separated as opposed to filtering or selecting the returned light collected by the detector. Thus, a tunable source delivers the information. Alternatively, both a tunable source and a tunable detector may be utilized. Such tuning takes the form of LCTF, acousto-optical tunable filter (AOTF), filter wheels, matched filters, diffraction gratings or other spectral separators. The light source may be a fiber optic, but is preferably a light emitting diode (LED) (see K. Gono et al., "*Appearance of enhanced tissue features in narrow-band endoscope imaging*" Journal of Biomedical Optics, 9(3):568-77, 2004; which is specifically incorporated by reference). This use is highly novel and is based on not just using LEDs as a broad light source, but rather specifically selecting LEDs to provide illumination specific for the chromophores of interest in a way such that the wavelength selector is no longer needed. LEDs and other system parameters could be selected to provide information about any compound with appropriate spectral characteristics in the wavelengths measured by the device, whether as a medical device or a device used in other applications such as environmental, food process control, pharmaceutical process control, geologic, military etc.

In one embodiment, such a device would be particularly well suited for use on the end of an endoscope, more preferably a disposable endoscope or other device where a low cost, proximal light source (as opposed to a distant source with a fiberoptic delivery system) would be an advantage.

The proposed instrument could be used as part of a remote device for either medical or other applications in an endoscope, laparoscope, boroscope or other rigid or flexible device for internal examination of the body or the internal surface of any structure such as an industrial pipe, or hard to reach location within machinery in order to augment available diagnostic or other data. In the case of an endoscope, laparoscope, boroscope or other rigid or flexible device for internal examination of the body or the internal surface of any structure such as an industrial pipe, or hard to reach location within machinery, the LED system described could be positioned at the operator end of the scope and transmitted to the end by fiber-optics. Alternatively, small LEDs could be positioned at the end of the scope for direct illumination of the ROI. In medical applications, such a scope could be used to assess systemic shock similar to skin readings presented here, or regional ischemia such as ischemic colitis or local disease such as cancer or polyps. Projection of the HSI image back onto the tissue facilitates diagnosis and targeted biopsy.

In another embodiment, the HSI instrument could be placed on a robot for remote sensing. In another application, lenses could be configured to collect data from a distance. LEDs, lasers or other illumination sources with long distance penetration or ambient light such as the sun can be used to illuminate the target. Any of these could be used independently, or different kinds could be used combined to deliver the total light used during data collection.

In such preferred embodiments, the HSI instrument is used as a non-contact remote means of assessing physiologic status in extreme environmental conditions simulated during hypovolemia induced lower body negative pressure. Preferably, vital signs are monitored by a non-technical provider wearing chemical/biological warfare (CBW) protective clothing to protect metabolic embarrassment and impending hemodynamic collapse. Such a system is advantageous in CBW.

Light could be collected from the skin of a person or the surface of an object through any substance transparent or partially transparent to the wavelengths being utilized. One embodiment of this could be for patient assessment through a protective mask used for protection from potentially harmful chemical or biological agents.

In another embodiment, whether with LED system or other (e.g. filter based) system employed, transmitted light as opposed to reflected light would be collected through a relatively thin piece of tissue such as a webspace between the fingers or toes or the ear lobe or cheek. In another embodiment a translucent, transparent or semitransparent film or other substance could be place on the skin to filter both illumination and reflection.

In another embodiment, the system and method could be utilized or adapted to record information from the skin or other tissue with the light source coming from tissue chemoluminescence, phosphoresecence, or fluorescence either intrinsic, or associated with an injected or applied fluorophore or phosphor. Such light emitting compounds could either be static or dynamic based on extant conditions, varying with temperature, moisture, pressure This would allow for better spatial resolution of deeper tissues. In another embodiment a specific absorber (such as indocyanine green, nanoparticles) or reflector of light (such as intralipid or microspheres) could be injected or applied.

The unique cooling illumination provided by the LED prevents overheating of skin or other tissue which may result in poor image resolution. Preferably, the LED provides sufficient light while producing minimal or no increase or a small known increase in skin or tissue temperature. This lighting system in combination with the polarizer allows adequate illumination while preventing surface glare from internal organs and overheating of skin or other tissue under examination.

Once the image acquisition interface 50 has stored images for all of the image planes specified by the diagnostic protocol chosen by the operator, the image acquisition interface begins processing these image planes based on the image processing protocol from the selected diagnostic protocol module 56N. Processing operations can include general image processing of combined images, such as comparing the relative amplitude of the collected light at different wavelengths, adding amplitudes of the collected light at different wavelengths, or computing other combinations of signals corresponding to the acquired planes. The computed image is displayed on the display 12. Other preferred embodiments include storing the computed image in the storage device 60 or printing the computed image out on printer 62 (see U.S. Pat. No. 4,885,634; which is specifically incorporated by reference).

In an alternative embodiment, diagnostic protocol modules 56, printer 62, display 12, or any combination thereof, may be omitted from portable device 10. In this embodiment, acquired images are stored in storage device 60 during the medical procedure. At a later time, these images are transferred via a communications link to a second device or computer located at a remote location, for example, hospital medical records, for backup or reviewing at a later time. This second device can have the omitted diagnostic protocol modules, printer, display, or any combination thereof. In another embodiment, the stored images are transferred from portable device 10, located in the clinic, via a communications link to a remote second device in real time.

In one embodiment, a numerical hyperspectral shock index is presented to an operator. This could be related to other vital signs which are also presented by the device or could be presented as the sole measurement. In an alternative embodiment, the data is reduced to a simple set of instructions or indicators. For example, based on the data, the device could simply show a green light for healthy, yellow light for needs resuscitative therapy and a red light for uncorrectable physiologic derangement.

In a preferred embodiment the system correlates the HSI data with the real source of presented data in real time or near-real time via a heads up display (HUD) or via projection. Preferably HSI projects real-time hyperspectral data onto the region of interest, or viewing window. The projected information has precise one-to-one mapping to the illuminated surface (e.g. wound, operating surface, tissue) and provides necessary information in an efficient manner. When projected onto an overhang viewing window preferably, the images (real-color and/or pseudo-color) can be zoomed in/out to provide variable magnification. This subsystem consists of the following elements: 1) image projector with field-of-view precisely co-aligned with the field-of-view of the hyperspectral imager, 2) miniature remote control device which allows the operator to switch the projected image on and off without turning from the ROI and change highlight structure and/or translucency on the projected image to improve visibility of the features of interest as well as projected image brightness and intensity, 3) real-time data processing package which constructs projected image based on hyperspectral data and operator/surgeon input, 4) optional viewing window positioned above the ROI that is translucent for real observation or opaque for projecting pseudo-color solution or higher resolution images.

To achieve precise co-registration between the hyperspectral image and the ROI, the system performs a self-alignment procedure as necessary. The system projects a sequence of calibration patterns on the operating surface using the projector and reads them using the hyperspectral imaging system. Calibration software processes acquired data and stores the data. Processed data are further used by the projection system to achieve high-precision mapping to the operating surface and to compensate for surface relief.

Such a projection system or the simpler camera system could also be utilized to evaluate the level of local tissue compromise or regional ischemia either because of local trauma, vascular compromise (i.e. where the leg is viable, needs vascular reconstruction or is not salvageable beyond a femoral artery injury). Regional or local vascular compromise could be on top of systemic aberrations due to shock, diabetes, congestive heart failure, etc. The projector could be used to determine level for amputation or assist with the geometry of a plastic surgical flap reconstruction.

Figure 2:
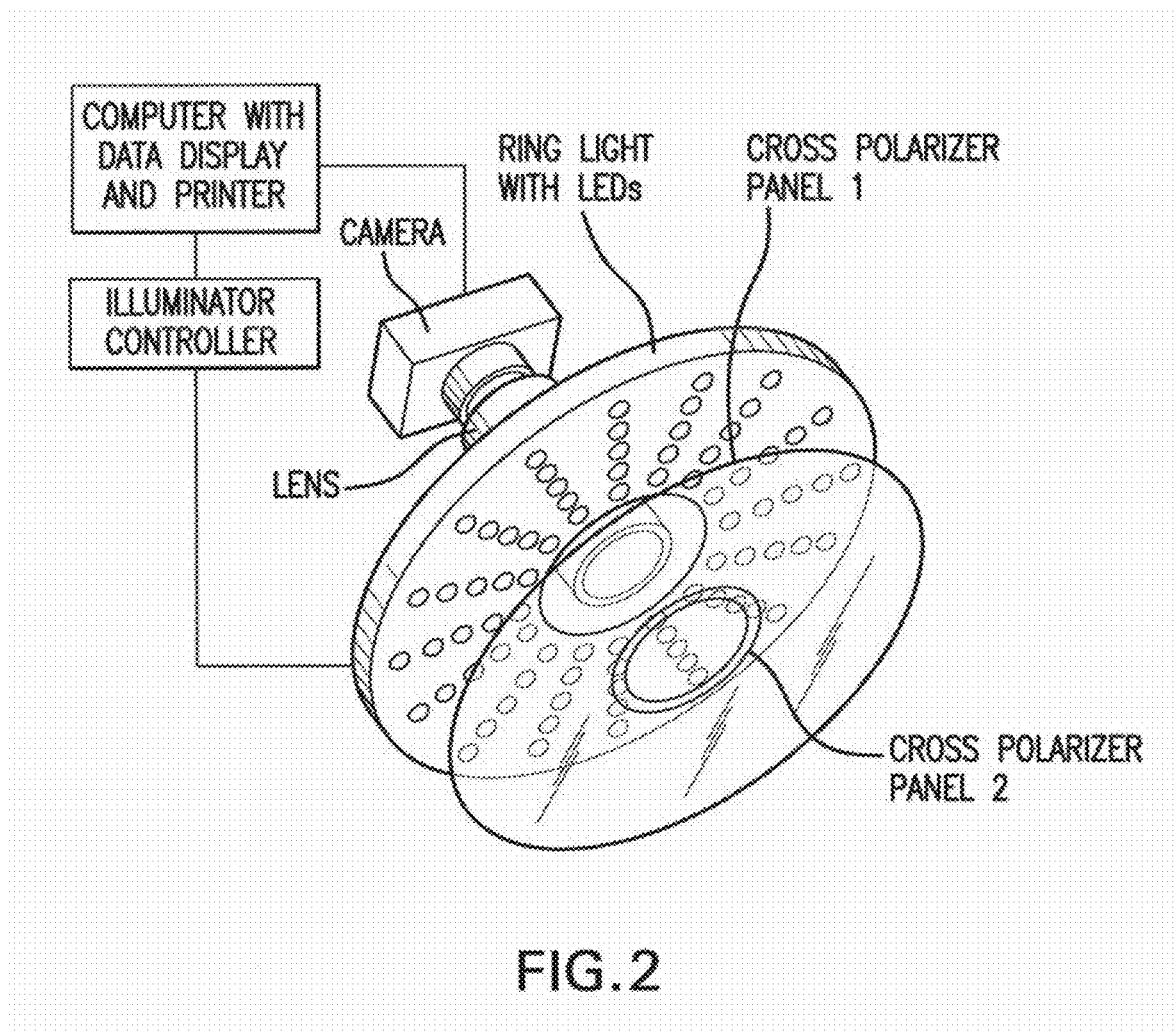
FIG. 2 HSI system with light of preselected wavelengths. Narrowband LED's can be used such that the spectral separator is no longer needed.

In another preferred embodiment, the hyperspectral system consists of a visible and NIR light sensor (camera), a lens tuned for visible and NIR wavelengths, illuminator with light controller, and computer running system control, data acquisition and preprocessing software as depicted in FIG. 2. The illuminator preferably consists of one or more sets of LEDs with different spectral properties of the emission. Each set has its own central emission wavelength and emission bandwidth. More preferably, each set includes LEDs distributed in a circular pattern around the lens, allowing for uniform illumination at each spectral point. Each set of LEDs is powered on and off by an "Illuminator Controller" controlled by the computer. Preferably, to decrease the effect of ambient light, the difference in intensity between two images is measured. One image is taken when a particular LED set is powered on, and the other image is taken when the set is powered off. Another preferred embodiment involves two apparatus of the invention, one with narrow band LEDs and the other with a filter.

An exemplary embodiment of a measurement sequence is as follows: turn first LED set on and acquire data turn off the LED set and acquire data; turn second LED set on and acquire data, turn second LED set off and acquire data; turn third LED set on and acquire data, turn third LED set off and acquire data; and so on as desired. The data, images of the object, are taken while illuminated by every set of LEDs in subsequent turns. Central emission wavelengths and bandwidth of LED sets are selected specifically such that combinations of images of the object taken as described above allow the calculation of the concentration of oxygenated and deoxygenated hemoglobin, and concentration of water in the tissue. Preferred central emission wavelength and bandwidths of LED sets are selected as follows:

| Set number | Central wavelength (nm) | Bandwidth (nm) |
| --- | --- | --- |
| 1 | 529 +/− 10 | 7 (3-20) |
| 2 | 542 +/− 10 | 20 +/− 10 |
| 3 | 562 +/− 10 | 45 +/− 30 |
| 4 | 577 +/− 10 | 15 +/− 10 |
| 5 | 960 +/− 20 | 20 (5-50) |
| 6 | 980 +/− 20 | 20 (5-50) |

To calculate concentrations of oxygenated, deoxygenated, and total hemoglobin, a linear combination and/or their ratio of images recorded from LED sets 1-4 is used. The intensities of LED sets 2 and 4 are adjusted in such way that the resulting emission spectra closely correspond to the absorption spectra of the oxygenated hemoglobin. The intensity of LED set number 3 is adjusted according to the absorption spectra of the deoxygenated hemoglobin at a similar concentration. The intensity of LED set number 1 is adjusted according to both, oxy- and deoxyhemoglobin spectra.

Preferably, intensities of the LEDs are set in house according to particular spectra. It is preferred that illumination intensity modulated to mimic spectra of deoxyHb and oxyHb. Variations may span from 1 to 100 nm, or more, but preferred variations are from 5 to 30 nm or from 10 to 60 nm.

Duration or exposure time varies according to sample. Accordingly, there is a learning or teaching aspect involved with each sample. For instance, characteristics of a skin sample including, but not limited to, hair, pigment and tone vary exposure time necessary for adequate signal-to-noise level of data. For an acceptable signal from darker skin, exposure time is usually longer than for fairer skin.

To calculate the concentration of water and its changes with time, a linear combination and/or their ratio of images recorded from LED sets 5-6 is used. The intensities of LED sets 5 and 6 are adjusted according to the absorption spectra of water at a concentration similar to the hemoglobin.

The light source preferably includes a polarizer disk in front of the LED lights that is cross-polarized (or at an angle) with its central disk that covers the lens. However, other embodiments may exclude the polarizer disk.

In another embodiment, the HSI system employs a liquid-crystal tunable filter (LCTF), placed in front of a standard lens and digital camera. By varying the voltage across the LCTF, the wavelength of light admitted to the camera is varied. During image acquisition, a hypercube of images, each at a separate wavelength, is generated (preferably at 5-20 nm intervals across 500 to 600 nm). Then, the visible light spectrum for each pixel in the hypercube is compared by linear regression to standard spectra for oxyhemoglobin (OxyHb) and deoxyhemoglobin (DeoxyHb). The resulting fit coefficients for OxyHb and DeoxyHb are used to calculate $S_{HSI}O_2$ values for each pixel in the ROI. The mean values for OxyHb, DeoxyHb, and $S_{HSI}O_2$ across the ROI are calculated. Grayscale $S_{HSI}O_2$ pictures of the ROI are also generated, in which the brightness of each pixel is proportional to its value.

Visible HSI provides improved signal-to-noise ratio over near-infrared spectroscopy for the measurement of hemoglobin spectra, since the hemoglobin absorption signal is much stronger in the visible than in the near-infrared range. While most of the NIR HSI information pertains to water content in the tissue, OxyHb and DeoxyHb information is also present. Utility of near-infrared point spectroscopy has been shown in its ability to provide information about sub-surface tissue oxygenation, for example in brain or muscle, and which derives from the increased tissue penetration of near-infrared light. By contrast, visible light spectroscopy, employed in preferred embodiments, interrogates hemoglobin saturation at a more superficial level, most likely within dermal capillaries. Thus, using HSI information from either visible and near infrared HSI together or visible HSI combined with NIR point spectroscopy provide potentially complementary information about different tissue beds, the visible light reporting on more superficial tissue and the NIR on deeper tissue. Comparing visible and NIR HSI data from a particular location may deliver useful information as to shock or regional or local tissue physiology. Further embodiments of the invention detect IR thermometer and IR themomatrix to record surface temperatures at the same time with VIS and/or NIR measurements.

The preferred embodiments and devices of the present invention allow for the creation and unique identification of patterns in data that highlight the information of interest. The data sets in this case may be discrete images, each tightly bounded in spectra that can then be analyzed. This is analogous to looking at a scene through various colored lenses, each filtering out all but a particular color, and then a recombining of these images into something new. Such techniques as false color analysis (assigning new colors to an image that don't represent the true color but are an artifact designed to improve the image analysis by a human) are also applicable. Optionally, optics can be modified to provide a zoom function, or to transition from a micro environment to a macro environment and a macro environment to a micro environment. Further, commercially available features can be added to provide real-time or near real-time functioning. Data analysis can be enhanced by triangulation with two or more optical acquisition systems or rotation or movement of a single system. Polarizers may be used as desired to enhance signatures for various targets.

In addition to having the ability to gather data, the present invention also encompasses the ability to combine the data in various manners including vision fusion, summation, subtraction and other, more complex processes whereby certain unique signatures for information of interest can be defined so that background data and imagery can be removed, thereby highlighting features or information of interest. This can also be combined with automated ways of noting or highlighting items, areas or information of interest in the display of the information.

The hyperspectrally resolved image in the present invention is comprised of a plurality of spectral bands. Each spectral band is adjacent to another forming a continuous set. Preferably, each spectral band having a bandwidth of less than 50 nm, more preferably less than 30 nm, more preferably less than 20 nm, more preferably, from about 20-40 nm, more preferably, from about 20-30 nm, more preferably, from about 10-20 nm, more preferably from about 10-15 nm, and more preferably from about 10-12 nm.

It is clear to one skilled in the art that there are many uses for a medical hyperspectral imager (MHSI) according to the invention. The MHSI offers the advantages of performing the functions for such uses faster, more economically, and with less equipment and infrastructure/logistics tail than other conventional techniques. Many similar examples can be ascertained by one of ordinary skill in the art from this disclosure for circumstances where medical personal relies on their visual analysis of the biological system. The MHSI acts like "magic glasses" to help human to see inside and beyond.

Data Acquisition and Data Pre-Processing

The first step in the invention is the creation of a hyperspectral data set from the measurements taken: the acquisition of the hyperspectral data cube, or hypercube. A region of the patient's skin or other tissue is selected for imaging, and a series of images are collected while illuminated by light at different wavelength ranges preferably (but not necessary) in turns with acquisitions without illumination. Preferably, the wavelength region used is between 450 and 1200 nm. In a preferred embodiment, the wavelengths collected include portions of the spectrum that provide a good discrimination between blood oxyhemoglobin and blood deoxyhemoglobin, or approximately 500-600 nm. In another preferred embodiment, the system also collects wavelengths, from a portion of the spectrum where water is highly absorbent, approximately 950-1100 nm as well as those that provide a good discrimination between blood oxyhemoglobin and blood deoxyhemoglobin, or approximately 500-600 nm. An "data image" associated with each separate wavelength band is collected. Data images from the spectral region are digitized using a recording camera, preferably a CCD or CMOS camera, and are recorded, forming a three-dimensional "data cube" (2 spatial dimensions and one wavelength frequency dimension).

Preferably, once a full set of spectral data images is acquired, the scanning process is repeated at a frequency sufficient to detect changes in metabolic status. Sequential data images are then collected into a four-dimensional "hypercube" (2 spatial dimensions by one wavelength frequency dimension and one time dimension).

Preferably, during the image collection, specified active illumination is provided. An important aspect of the illumination is that it should not result in substantial heating of the patient's skin or tissue. Preferably, as part of the data collection, an image is taken of a white reflector affixed to the subject's skin. This provides a calibration image that is used to calibrate for uneven illumination effects and provides a reference for calculating optical absorption.

The data pre-processing described herein is preferably performed by the MHSI system and more preferably it is part of a shock diagnostic module. Such a module could be automatic in the device or could be selected by the operator from a menu of modules for different applications. Preferably, different diagnostic modules all relevant to shock could also be in place for choice by the operator under different patient conditions, environmental conditions or other circumstances.

While not necessary, preferably any of the following pre-processing steps are implemented and more preferably, they are all implemented as described.

Preferably, the first step in data pre-processing is removing the ambient light contribution and evaluating reflected intensity per unit time. This is performed by subtracting an image recorded without the LED or other administered light from an image recorded with the light, for each wavelength set. The resultant image is normalized by the exposure time that is preferably the same for both images, with and without the administered light:

HSI Intensity=Intensity with light/exposure time− Intensity without light/exposure time Preferably, this is performed for the ROI or a portion of the ROI. More preferably, it is performed for each pixel or region of pixels. Preferably, under weak ambient light conditions, the correction for dark noise, read-out noise, background radiation, and similar distortion sources is performed instead.

Preferably, the second step in data pre-processing is to calculate optical absorption as a decimal logarithm of the ratio of the derived normalized HSI image intensity to the reference normalized intensity recorded off the white reflector:

Absorption=log$_{10}$(HSI Intensity/Calibrator Intensity)

This is performed for each pixel or region of pixels. Preferably, the Calibrator Intensity is recorded during data acquisition and/or prior and stored in the HSI system for subsequent data pre-processing.

Preferably, the third step in data pre-processing is to perform image registration at each time step. Registration causes the images acquired at different time to be translated, rotated and scaled such that distinctive features in the images captured at each moment lie at the same spatial location in each image. Image registration is especially important for patients in or near shock, as the patient may move due to pain and discomfort or involuntarily. If desired, a calibrator or small registration mark may be applied to the skin to provide a distinctive feature for registration algorithms. The problem of image registration is discussed in more detail by Freeman et al. in U.S. Patent Application 20040236229 and U.S. Provisional Application 60/717,188.

Figure 3:
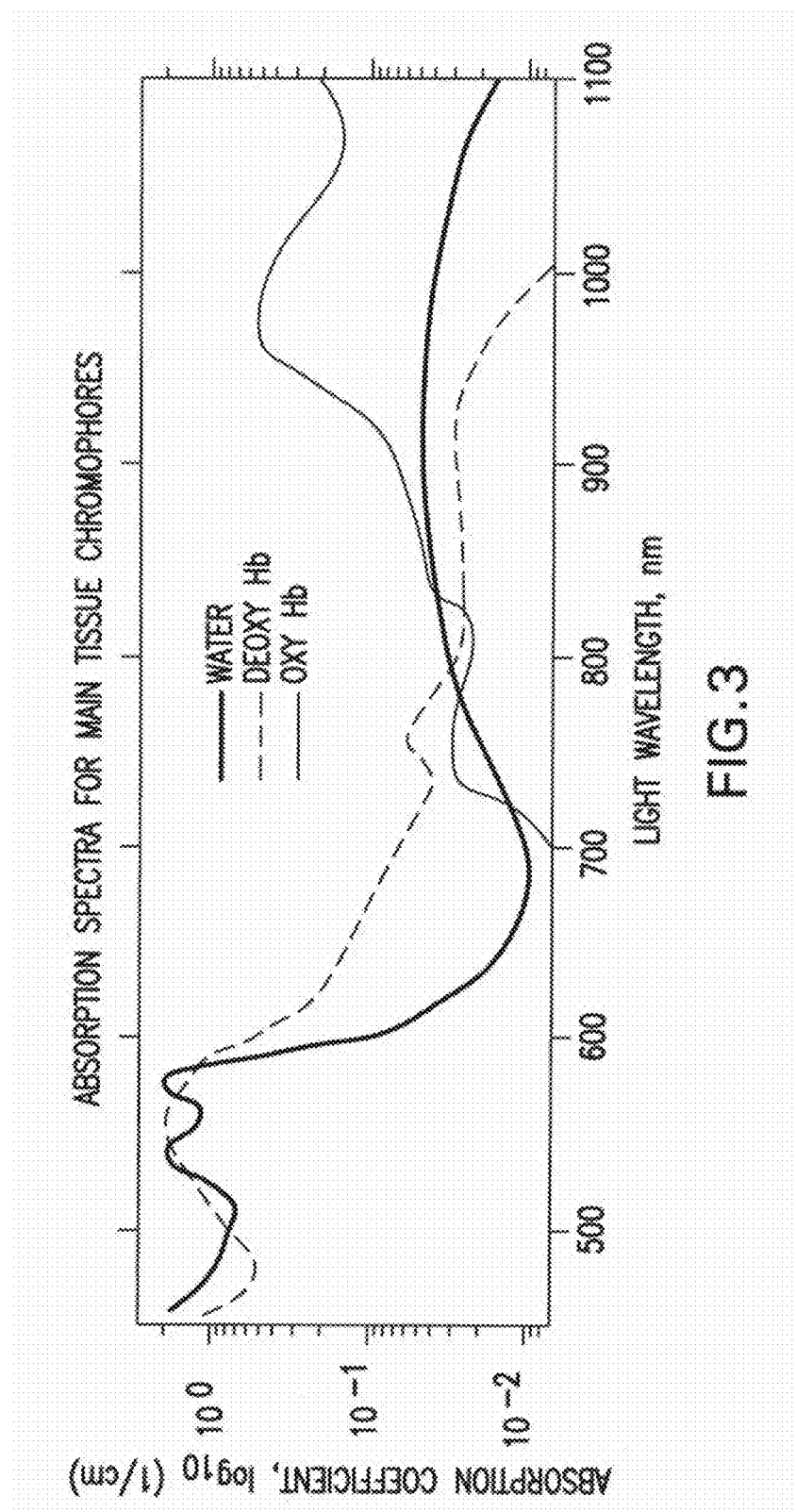
FIG. 3 Visible and NIR absorption spectra of main chromophores of skin: water (thick line), oxygenated hemoglobin (thin line), and deoxygenated hemoglobin (dashed line).

Once images are captured and pre-processing is completed, preferably, the next step in data processing is to decompose the data to provide an estimate of the chemical signatures present in each pixel of the image. This decomposition step requires, in addition to the hyperspectral data, a reference spectrum for each chromophore (i.e. tissue or fluid) of interest. For example, spectra captured for blood oxyhemoglobin, blood deoxyhemoglobin, and water can be used in the decomposition process (see FIG. 3).

Figure 4:
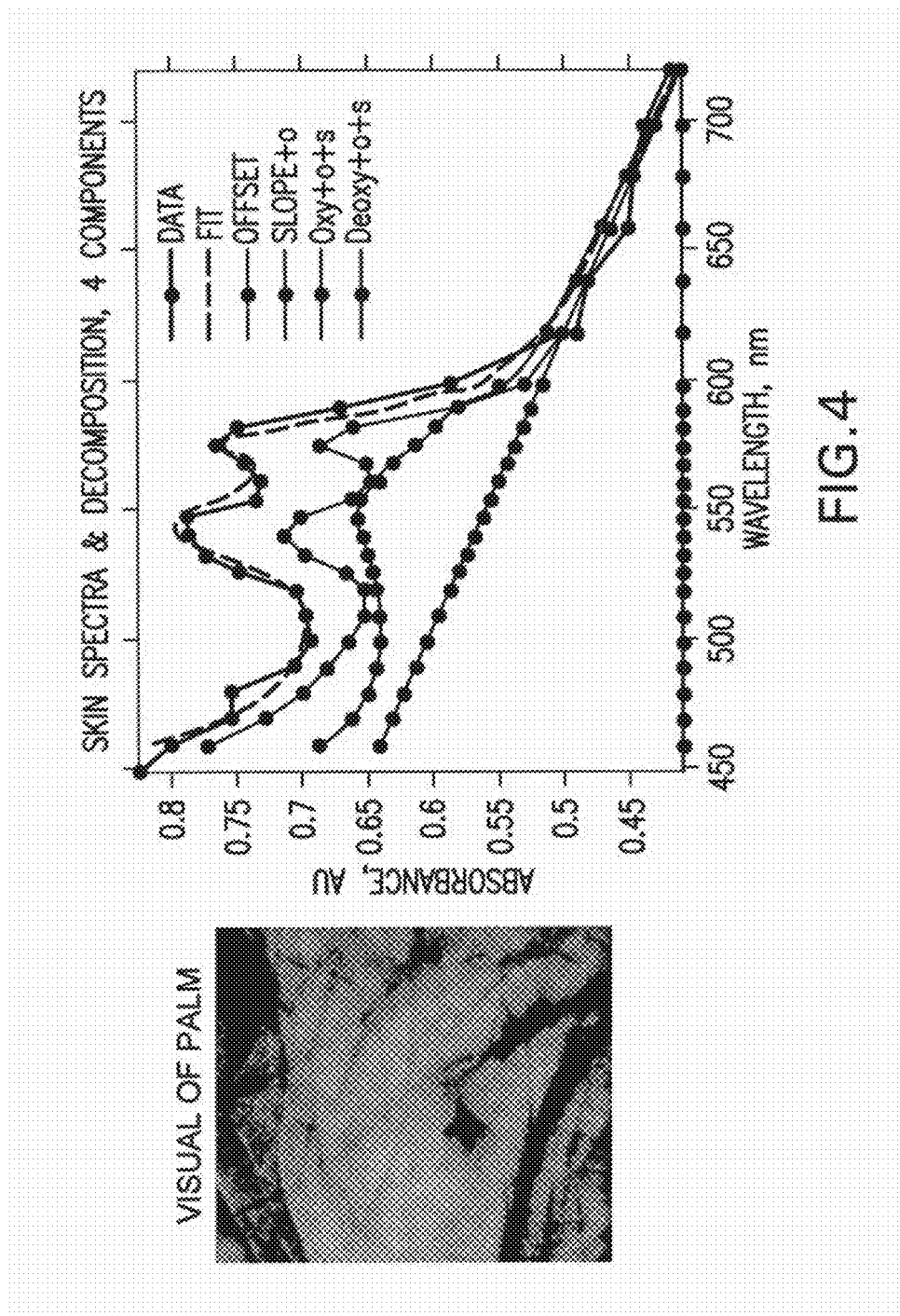
FIG. 4 Using visible MHSI, a color image for a palm (left panel) and spectra (right panel) was recorded at one pixel of the hypercube. The recorded spectra (black solid line) are decomposed into four components (offset, slope, oxy, and deoxyhemoglobin), such that when composed back, they form a line (black dotted) fitted to the real data in a least-square sense.

If hyperspectral data were recorded using the system with a light separator (FIG. 1), each pixel in the hypercube has skin absorption spectra (somewhat similar to the spectra in FIG. 4). The decomposition process then can be generally framed as a constrained optimization problem, in which the relative abundance of each chemical species is estimated subject to constraints on the physically possible range of abundance values [16]. However, a straightforward and robust decomposition can be obtained using a least-squares solution (for each pixel or a region of pixels):

$$S_{ij}(\lambda) = \|c_{1ij}\text{OxyHb}(\lambda) + c_{2ij}\text{DeoxyHb}(\lambda) + c_{3ij}\text{Water}(\lambda) + c_{4ij} \times \lambda + c_{5ij}\|_2$$

The decomposition results in the output images of estimated abundance for each of the chemical species considered (in the example above, $c_1$ and $c_2$ are images for oxy and deoxyhemoglobin concentrations, whereas $c_3$ is for the water). The slope and offset are denoted by $c_4$ and $c_5$, respectively.

In the embodiment where hyperspectral data is recorded using the system with specifically selected and/or modulated light (FIG. 2), the data images recorded with light from each LED set represent the concentration of chromophores integrated over that wavelength range. For example, when the white reflector is illuminated with the LED sets 2 and 4 (that are preferably chosen and modulated to mimic or partially mimic the oxyhemoglobin absorption spectra), the recorded data image represents the HSI system response to illumination, integrated over the entirety of the LED set 2 and 4 wavelength range. When the skin is illuminated with the LED sets 2 and 4, the recorded data image differs from the data image acquired off the calibrator by the amount of skin oxyhemoglobin absorption integrated over the entirety of the LED set 2 and 4 wavelength range. The skin data image referenced to the calibrator data image has information on skin absorption due to oxy-hemoglobin in addition to slope and offset components. Similar steps are taken with illumination with the LED set 3, where the skin absorption due to deoxyhemoglobin in addition to slope and offset components is recorded. The skin response to the LED set 1, where both oxy- and deoxyhemoglobin have same absorption under similar concentrations, determines the total hemoglobin concentration in the skin. Difference between data images from sets 1, 2, 3, and 4 allows the elimination of the slope and offset spectral components and the identification of the oxy- and deoxyhemoglobin concentrations. And finally, the skin response to LED sets 5 and 6 and the difference between the two, determines the water concentration and allows the assessment of tissue hydration levels.

Data from any or all of the described LED sets may be utilized to evaluate a given physiological state. Or any or all of the described LED sets may be used in combination with other spectral separation techniques to collect data in similar or other parts of the spectrum. For example, a visible LCTF system could be used in concert with an LED system similar to LED sets 5 and 6 to augment information provided by the visible spectrum such as hemoglobin with infrared data regarding water concentration.

For the present invention it is preferred that at least tissue oxyhemoglobin and deoxyhemoglobin be calculated or estimated (other quantities such as water abundance can also be utilized). Denoting these estimated abundances as OxyHb and DeoxyHb respectively, the blood total hemoglobin (THb) can be found from:

THb=OxyHb+DeoxyHb.

Relative tissue oxygen saturation ($S_{HSI}O_2$) can be found from:

$S_{HSI}O_2$=OxyHb/THb*100.

Note that these quantities (THb and $S_{HSI}O_2$) are by-products of the hyperspectral decomposition, and are calculated as they have relevance to similar measurements that are commonly referenced in the medical literature. Also, the hyperspectrally-derived data images may be clipped to remove extreme values. Smoothing with a low-pass filter (such as a Gaussian filter) may be used to enhance the data image before metrics are calculated from the data image.

Next, in one application of the invention to the assessment of shock, an index that reflects clinical signs of shock or impending shock are derived. Additional steps of analysis are performed across all or a portion of the ROI, including but not limited to calculation of a mean index, heterogeneity index, mottling index, temporal index, and combinations thereof. Preferably any or all of the first three algorithms that follow are used to derive these shock related indeces. A fourth algorithm describes likely patient outcomes or the severity of the shock response: reversible versus irreversible shock.

Algorithms

The first algorithm quantifies the markers that reflect clinical signs of shock that are characteristic to the entire image, or to the entire ROI, e.g mean and spread of the hyperspectral measurement across all or a selected portion of the ROI. For example, an early clinical sign of hemorrhagic shock is a drop in the total blood volume and therefore to the blood supply and blood oxygenation in the skin, particularly in the peripheral parts of the body. This results from both blood loss and the body's attempt to compensate for shock, hypovolemia or blood loss by restricting blood flow to peripheral parts of the body. This often leads to an overall drop in the amount of total blood and of oxygenated blood available to the areas being imaged during patient monitoring of shock. Conversely, associated with low flow to the skin there is greater extraction of oxygen from the limited amount of blood available and hence a relative increase in deoxyhemoglobin. Given the total decrease in all forms of hemoglobin, this relative increase in deoxyhemoglobin may lead to either an increase, decrease or similar levels of total deoxyhemoglobin prior to or in association with the onset of shock.

To derive mean values for a given ROI, changes in the overall quantities of blood and/or tissue oxygen delivery, oxygen extraction, oxygen saturation, total hemoglobin, or water content can be calculated directly by calculating quantities such as the mean, median, or fixed percentile measure of values on the hyperspectral data image. For this application a single number is derived from each component data image. The advantage of a data image over a point measurement for this case is that the integration provided by the large number of points being averaged results in a more accurate estimate.

Figure 5:
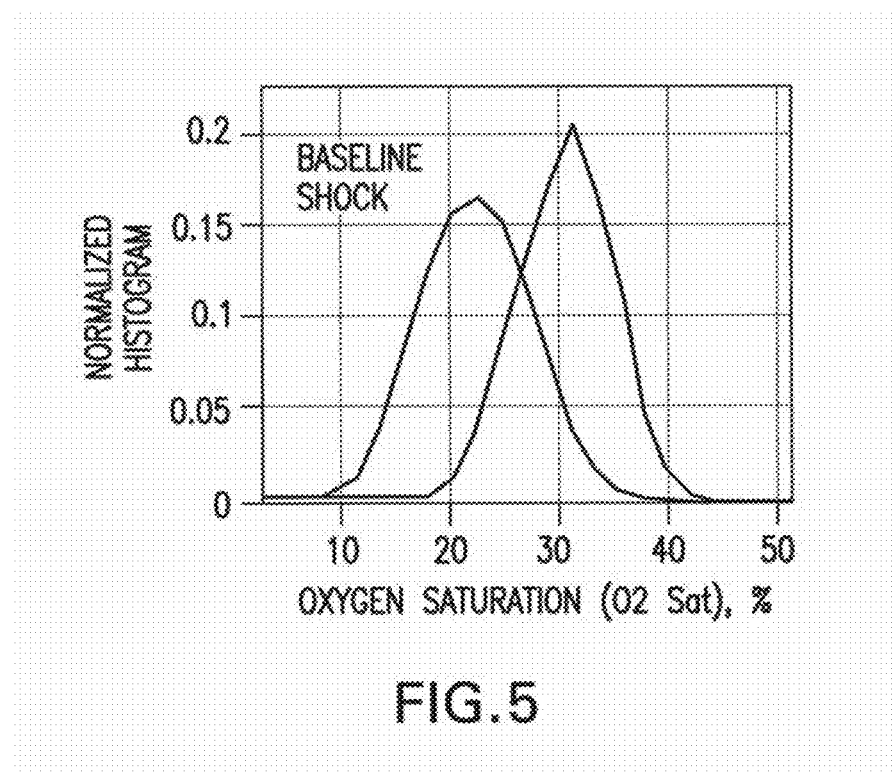
FIG. 5 Histograms of pixel intensity in $S_{HSI}O_2$ image for a porcine subject. The lines show the distribution of $S_{HSI}O_2$ values in skin at baseline and during shock. Reduction in the mean value provides a clear cue of shock.

FIG. 5 shows data results from an example porcine subject. Histograms are formed for hyperspectrally-calculated images of oxygen saturation taken at baseline and during shock. The histograms show that the reduction in the mean value of the oxygen saturation provides a cue as to circulatory shock for this subject.

Figure 6:
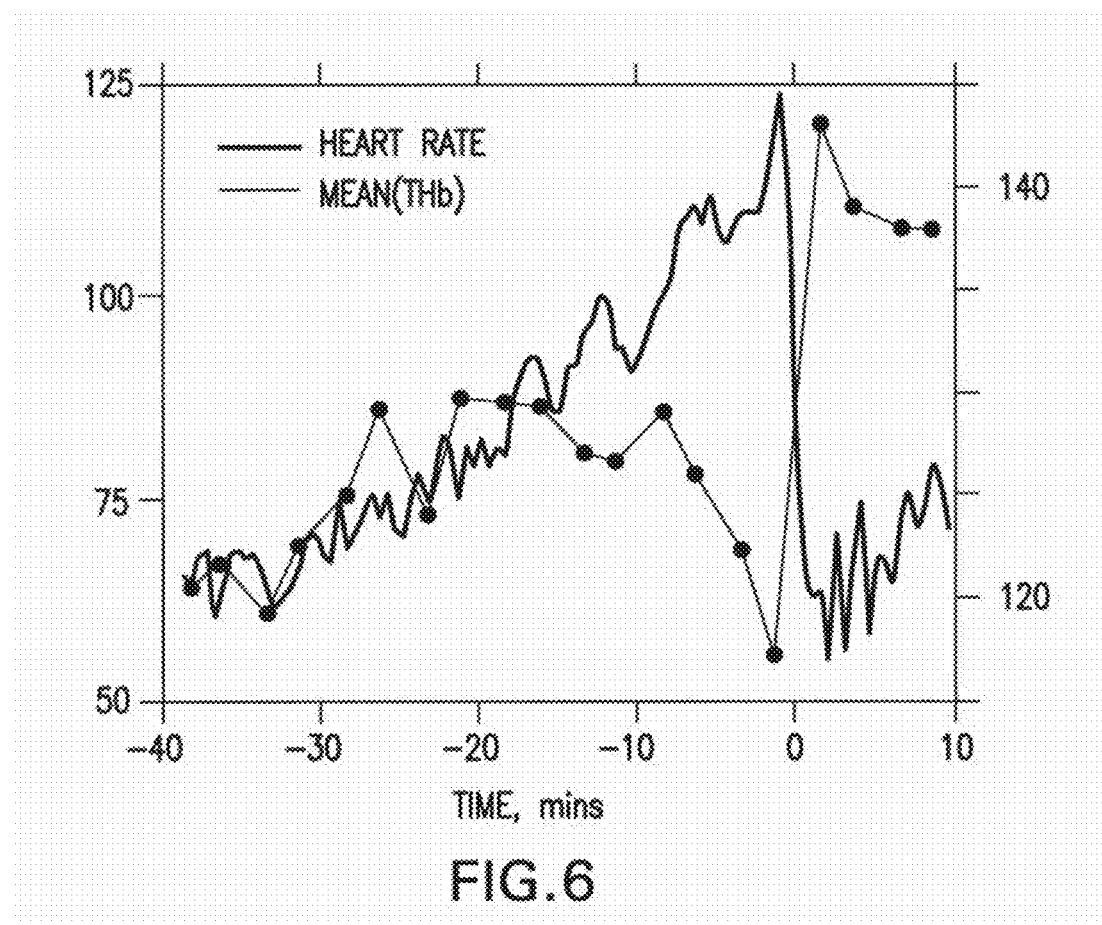
FIG. 6 Heart rate and mean THb (total hemoglobin averaged over ROI) during LBNP experiment for a human subject while pressure was reduced up to −90 mmHg. Syncope and return to zero LBNP occur at t=0. Total Hb drops precipitously prior to collapse.

FIG. 6 shows data results from an example human subject. The total hemoglobin drops precipitously prior to collapse.

If circumstances permit, it is possible to obtain baseline readings from the patient when he is clearly not in a state of shock. In this case, changes in average oxygenation, etc. may be referenced to the baseline state. When possible, use of a baseline is beneficial as it helps to remove patient-to-patient variations. Even without a baseline, trending of sequential measurements can provide important information. In emergency settings it may not be possible to obtain a baseline, and judgments about shock detection are made on raw (un-normalized) quantities or referred to a standard baseline derived from multiple other individuals.

Figure 8:
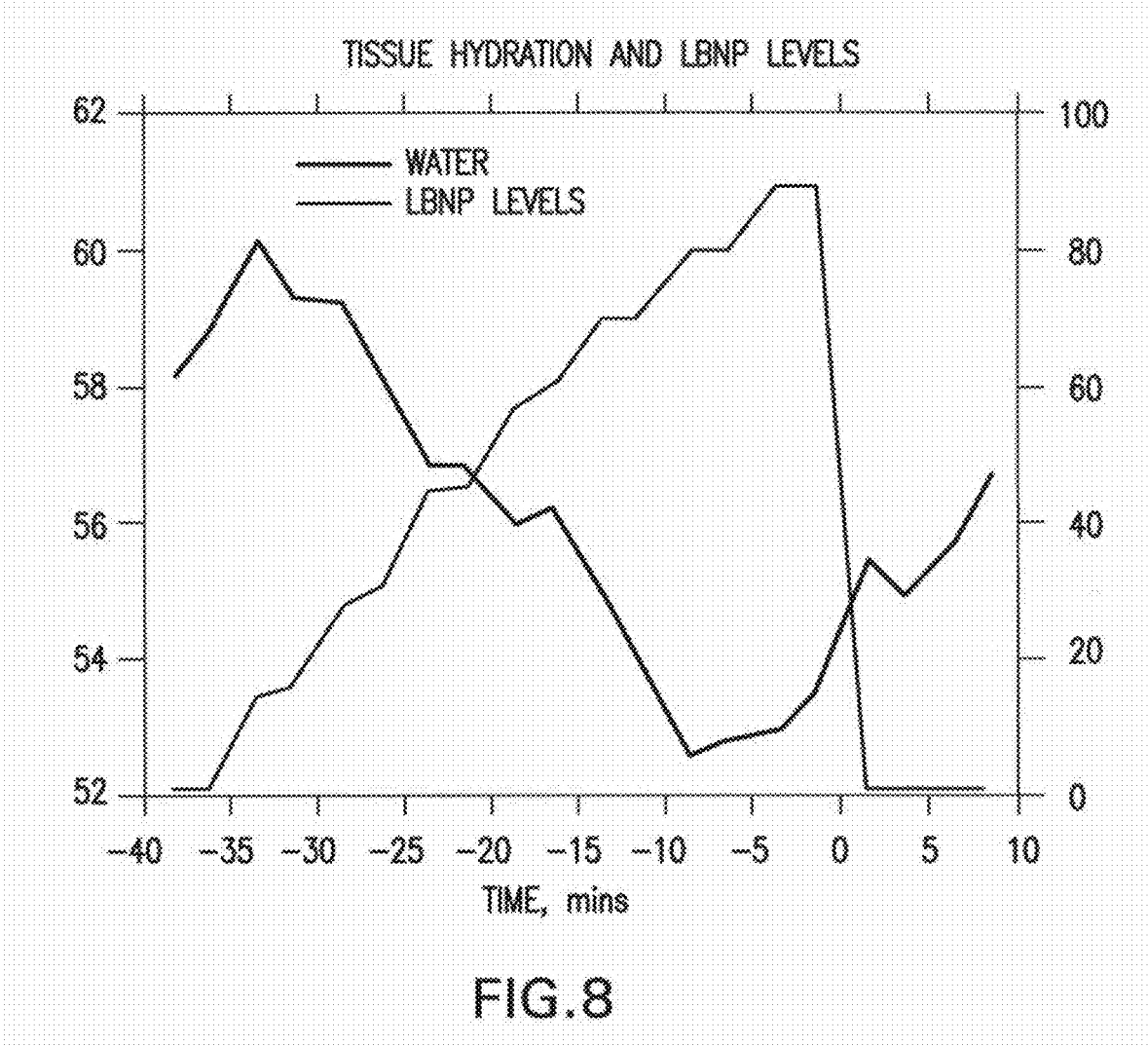
FIG. 8 Skin hydration averaged across ROI and LBNP during LBNP experiment for a human subject while pressure was reduced up to −90 mmHg. Syncope and return to zero LBNP occur at t=0. In this study, tissue hydration dropped by nearly 10 percent prior to collapse.

The water content, evaluated from the skin absorption in the NIR region (950-1100 nm) changes as a human subject undergoes reduction in the lower body pressure. FIG. 8 shows that water concentration in tissue drops by nearly 10 percent prior to collapse. Similar to total Hb and the standard deviation of oxygen saturation measured in the visible range, water is also one of the most effective markers that predict shock since significant change occurs well before the collapse (10 minutes in this case). Water is measured in near IR, which is more favorable in the battlefield.

In addition to the changes in the mean values of components: hemoglobin, oxy-, deoxy-, $S_{HSI}O_2$ and $H_2O$ in the data images, the spread and/or standard deviation in the component data images change. These changes relate to the increased presence of heterogeneous patterns in skin oxygen delivery/extraction and hydration in association with shock or hypovolemia.

Figure 7:
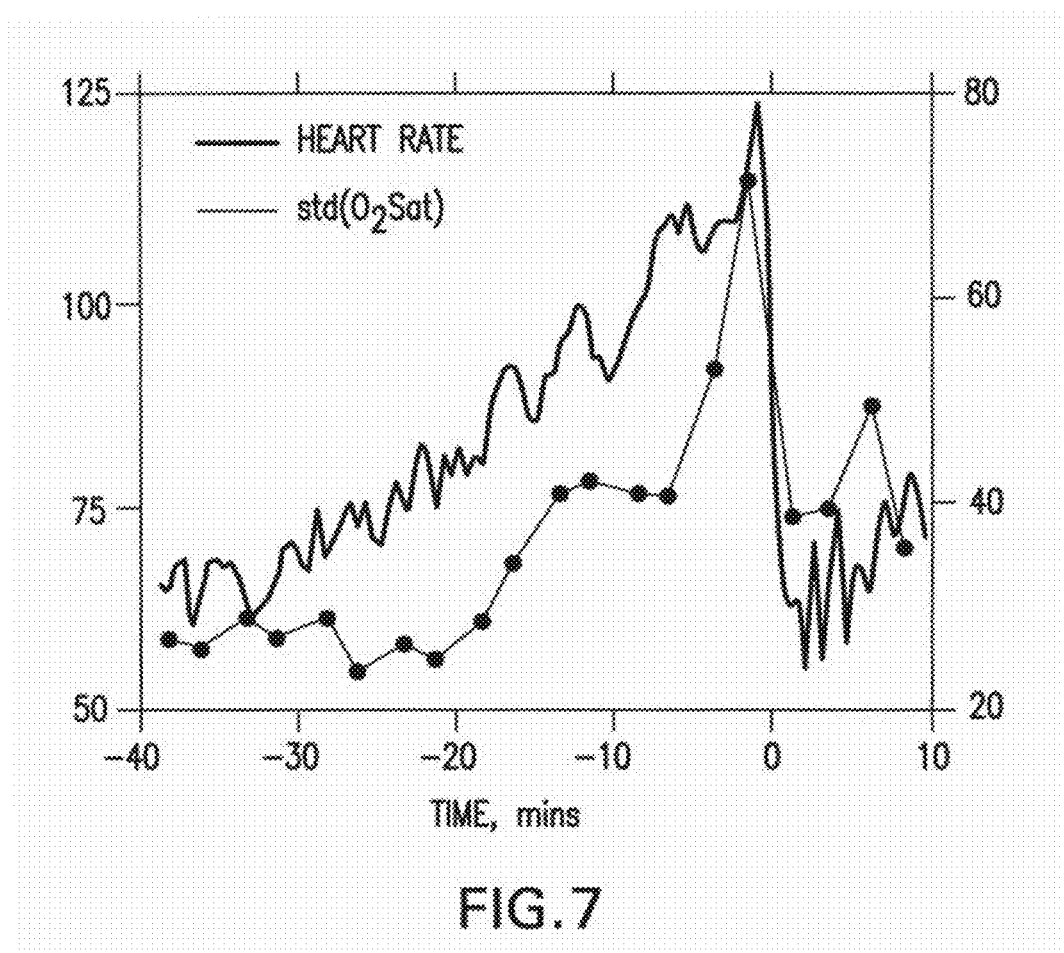
FIG. 7 Heart rate (red) and std($S_{HSI}O_2$) (standard deviation of $S_{HSI}O_2$ over ROI) (blue) during LBNP experiment for a human subject while pressure was reduced up to −90 mmHg. Syncope and return to zero LBNP occur at t=0. $S_{HSI}O_2$ heterogeneity rises prior to collapse.

FIG. 7 shows data results from an example human subject. The heterogeneity in the $S_{HSI}O_2$ images rises prior to hemodynamic collapse.

The second algorithm quantifies the markers that reflect clinical signs of shock and are related to more localized changes in oxygen delivery/extraction, e.g. mottling of the skin. Unlike point measurement of oxygenation, hyperspectral imaging is able to capture information about these mottling patterns. The presence of mottling can be detected and the mottling patterns can be characterized using a variety of image processing algorithms. Four separate methods for detecting and evaluating the mottling and its changes are described below.

As a first method to assess mottling, the size of mottling pattern can be determined. As mentioned earlier, the heterogeneity of the entire HSI image increases as shock approaches. nears. Measures of the increased heterogeneity, such as the standard deviation (std) or percentile-based measures of the spread (c.f. the difference between 75th and 25th quartile values of the image) can be evaluated at regions of smaller size. When the region of interest is comparable to the mottling pattern size, the spread within the region could drop (compare to the increased std over the entire image), reflecting homogeneity within the mottling area. The change in heterogeneity as a function of ROI size can be used to evaluate size of the mottling patterns.

As a second method for characterizing mottling, the mottling size and shape can be characterized using a measure of image complexity. Preferably this could utilize area-to-perimeter measurements for regions with high values. More preferably, the data images described above (oxygenation, etc.) can be processed via image processing techniques to yield a binary image describing "high" and "low" regions of the response. This binary image can be created using several approaches. In one embodiment, edge detection approaches are used to identify regions of interest. These edges are then filled in to form a binary image. In a second embodiment, the image is first filtered to remove low-frequency variation. A threshold for the filtered image is then determined, using Otsu's method or comparable threshold techniques. The threshold is used to identify "high" and "low" regions in the binary image.

Once a binary image is created, the area and summed perimeter of all "high" regions can be found. The ratio of these parameters gives a measure of mottling. If large, "bloblike" mottled regions exist in the imaged area, they will tend to have lower perimeter-to-area ratios. If the imaged area is relatively homogenous, "high" and "low" regions will tend to be small, corresponding to small regions of excursion from the local background. Thus the average perimeter-to-area ratio for these smaller regions is less than in a mottled subject.

Figure 9:
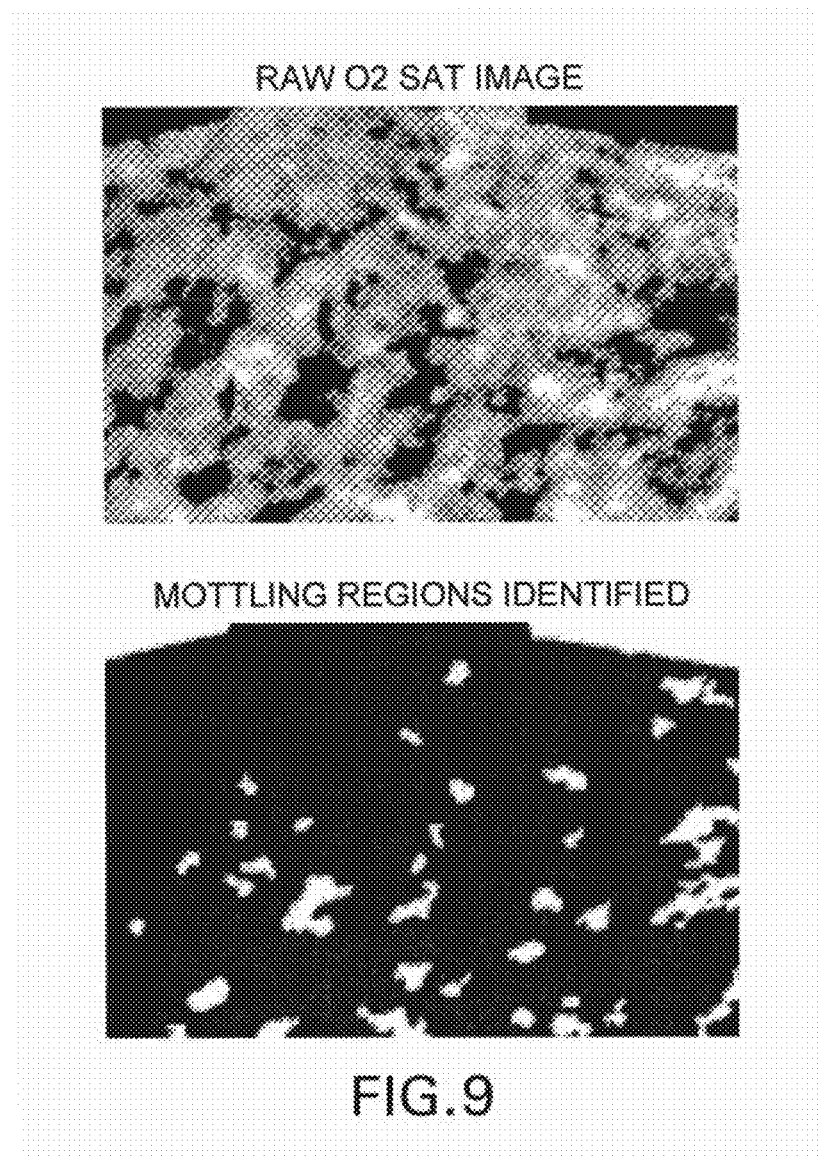
FIG. 9 Raw and processed images showing how image filtering can be used to give automated detection of skin mottling.

As a third method for characterizing mottling, image filtering can be used to enhance contiguous regions that deviate significantly from the mean. This approach takes advantage of two aspects of mottling; first, that mottled regions often have oxygenation or other values that differ significantly from the mean, and second, that mottled areas are typically larger rather than smaller. In the approach, a binary image is first formed that identifies all pixels in the hyperspectral image that differ from the mean by more than a user-specified amount. As an example, regions can be identified that are either 1) greater than the mean plus some multiple of the standard deviation or 2) less than the mean plus some multiple of the standard deviation. The method does not explicitly require use of the mean; for example, deviation from a low-frequency filtered version of the image may be used. This first binary image identifies regions with extreme values. As a second stage, the binary image is filtered to remove pixels that are not connected to at least N other pixels, where N is a user-selected parameter chosen to represent the smallest physiologically reasonable size for a mottled area. This second step results in a binary image of connected pixels that differ significantly from the mean, i.e. mottled regions. The area of all such regions is then summed to yield a metric representing the degree of mottling in the image. An example of this method is shown in FIG. 9.

As a fourth method for characterizing mottling, the degree of mottling change over time in a data image or an image of physiological parameters (such as blood oxygenation or saturation, or hydration state) is evaluated. This approach exploits the fact that the physiological parameters being imaged by the hyperspectral system change dynamically as the body attempts to compensate for shock. Skin mottling patterns shift to protect tissue viability in regions of vasoconstriction and these shifts occur more rapidly in advance of or with the progression of shock.

Figure 10:
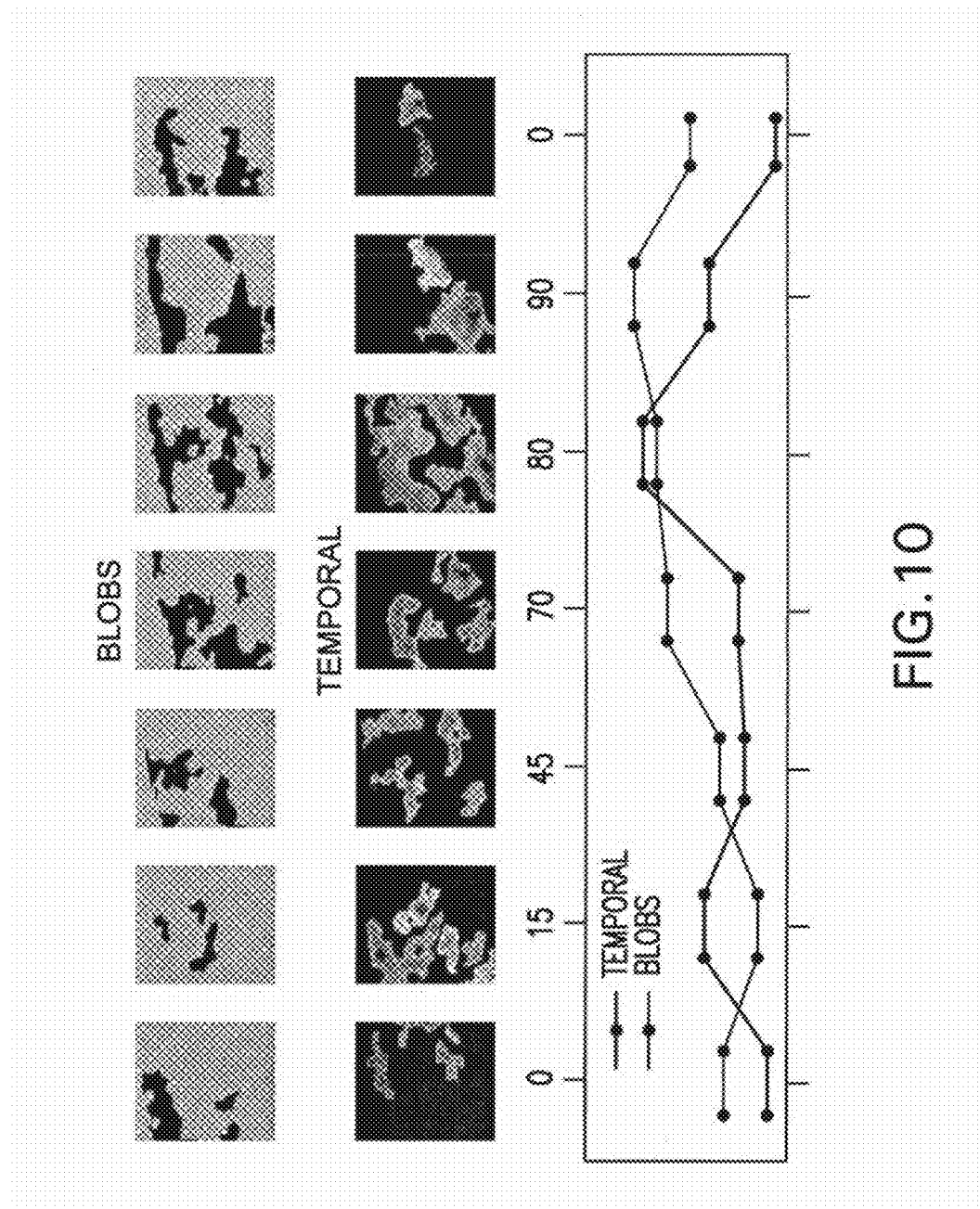
FIG. 10 The BLOBS and TEMPORALS (lower panel) characterize features in the images. BLOBS quantifies "mottling" or "blobbiness"—a large spatial variation in $S_{HSI}O_2$ that appears in association with shock. TEMPORAL quantifies the temporal change in "mottling" pattern from one time point to the next. In many instances, an increase in TEMPORAL precedes an increase in BLOBS.

Preferably, two parameters are derived to measure mottling variability, "blobbiness" and "temporal". To characterize these, the hyperspectral image is preferably converted to a 3-value image of "high", "low", and zero values (see top raw of plots in FIG. 10, where green is zero, red and blue correspond to "high" and "low" values in $S_{HSI}O_2$, correspondingly). Each plot in the raw corresponds to a particular time within the experiment, starting with baseline and progressing toward shock (image before last with the LBNP=−90) with the last image is back to equilibrium. The blobbiness represents the blob size, and it is calculated as sum of red and blue pixels, and is reduced to one number that is increasing with time towards collapse (green line in the lower panel, FIG. 10).

The temporal parameter that measures mottling variability is based on comparison between two sequential images of any or all of the HSI-measured or derived quantities. Preferably, these include but are not limited to OxyHb, DeoxyHb, THb, $S_{HSI}O_2$, water and single wavelength images,) either independently or in combination. More preferably, it includes but is not limited to OxyHb and DeoxyHb data images. The image later in the sequence is registered to the the previous, then subtracted from the previous (or vice versa) and the resulting image is analyzed. As an example of such an analysis, here the areas with little change (e.g. less than 1 standard deviation) are assigned to zero (dark blue in the second raw of plots in FIG. 10). The areas that have a positive change (e.g. increasing oxygenation) are colored with the shades of red while the negatively changed areas (e.g. reducing oxygenation) are in shades of blue. The areas (both, positive and negative) are then scaled with their maximal amplitude and summed over the entire image. Thus, the temporal variability in mottling is reduced to a single number that can be plotted as a function of time (see blue line in the lower panel in FIG. 10). In many instances, an increase in temporal component (blue line) precedes an increase in the blobbiness component (green line). The level of temporal and blobbiness components provides a measure of how rapidly the subject is reacting when attempting to compensate for shock, and is an indicator of physiological stress. Preferably one or more of these four methods are utilized to assess mottling. More preferably, more than one of these methods are combined to calculate a mottling index. Most preferably, blobbiness and temporal methods are combined to calculate a temporal mottling index.

The third algorithm for detecting shock combines the two previously described algorithms: the entire image analysis and the local mottling analysis. All markers quantified above that reflect clinical signs of shock are reduced to single values that change with time depending on physiological and metabolic state of the subject. Linear and non-linear compilation of these data approximates a HyperSpectral Shock Index (HSSI) measurement for the particular subject. As an example, using a relative HSSI scale where a measurement>1 is considered to be an index of shock, evidence of impending vascular collapse can be seen on a plotted graph using peaks and falls. HSSI acts as a very sensitive metric of circulatory regulation and goes up when there is an initial systemic compromise due to rising LBNP level and then back down as compensatory mechanism occurs.

Figure 11:
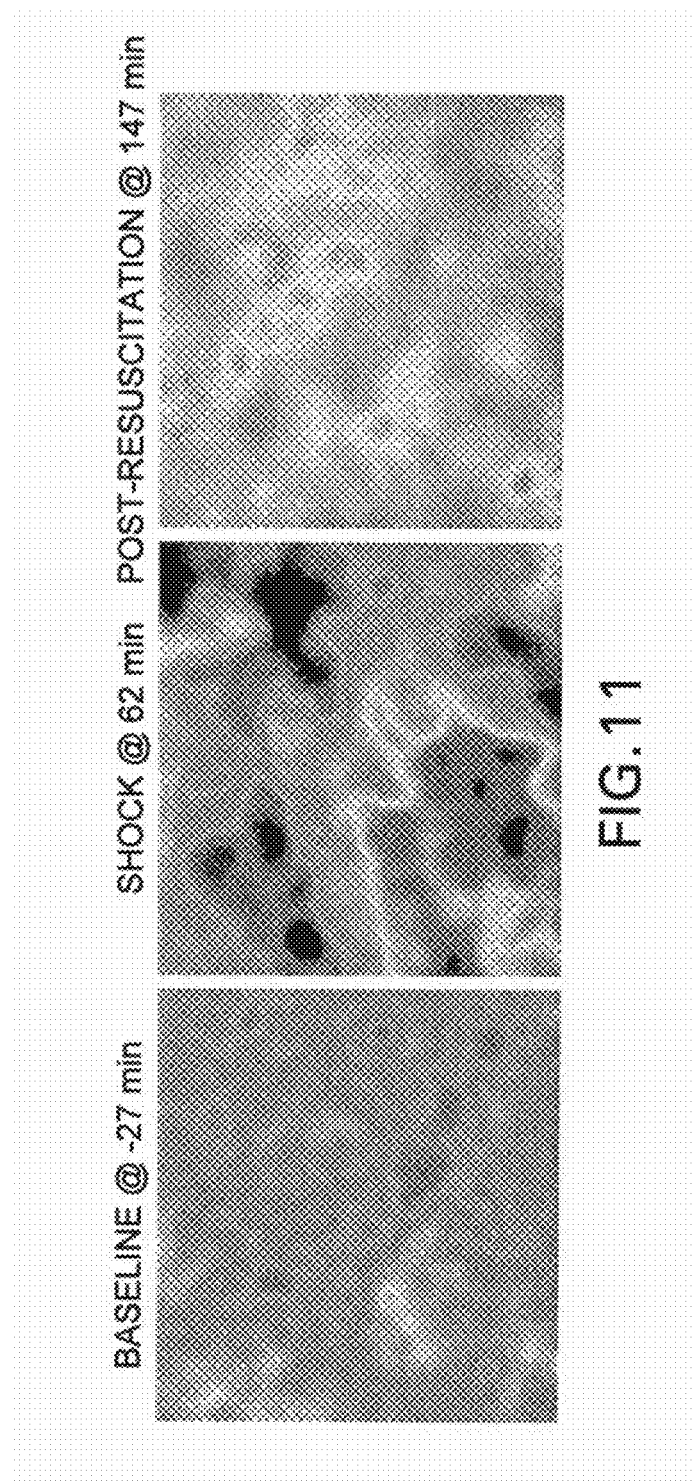
FIG. 11 MHSI oxyhemoglobin (OxyHb) reveals changes in circulatory patterns that are indicative of patient survivability. The OxyHb images show changes over the course of the animal shock experiment: left is at baseline (prior to the first bleed), middle is during the shock period (62 minutes after the first bleed), and right is at post-resuscitation equilibrium (147 minutes after the first bleed). Other pigs demonstrated complete recovery of baseline patterns post resuscitation.

The final algorithm describes methods for detecting features in the image that may indicate likely patient outcomes or the severity of the shock response: reversible versus irreversible shock. Previously described herein, measurements support early detection of shock, by uncovering homogeneous changes and mottling of the skin. Studies to date have also shown that hyperspectral images, by revealing changes in the microcirculatory patterns in the skin, can give cues as to patient survivability. FIG. 11 shows example hyperspectral oxyhemoglobin images for a porcine subject before bleed (left panel, 27 minutes prior), during shock (62 minutes after the first bleed), and post resuscitation (2 hours after the first bleed). The subject had developed large, rapidly changing mottling patterns that were associated with alternating high and low oxyhemoglobin levels. The circulatory pattern has recovered post resuscitation (compare third and first image in FIG. 11). Another animal subject (FIG. 12) had developed a distinctive "feathery" pattern in the $S_{HSI}O_2$ images. This pattern developed in many of the test subjects that either died during the procedure or did not exhibit strong recoveries to the test procedure, and appears to indicate a higher likelihood of an unfavorable outcome. Presenting such a cue to medical personnel could be of great value.

Figure 12:
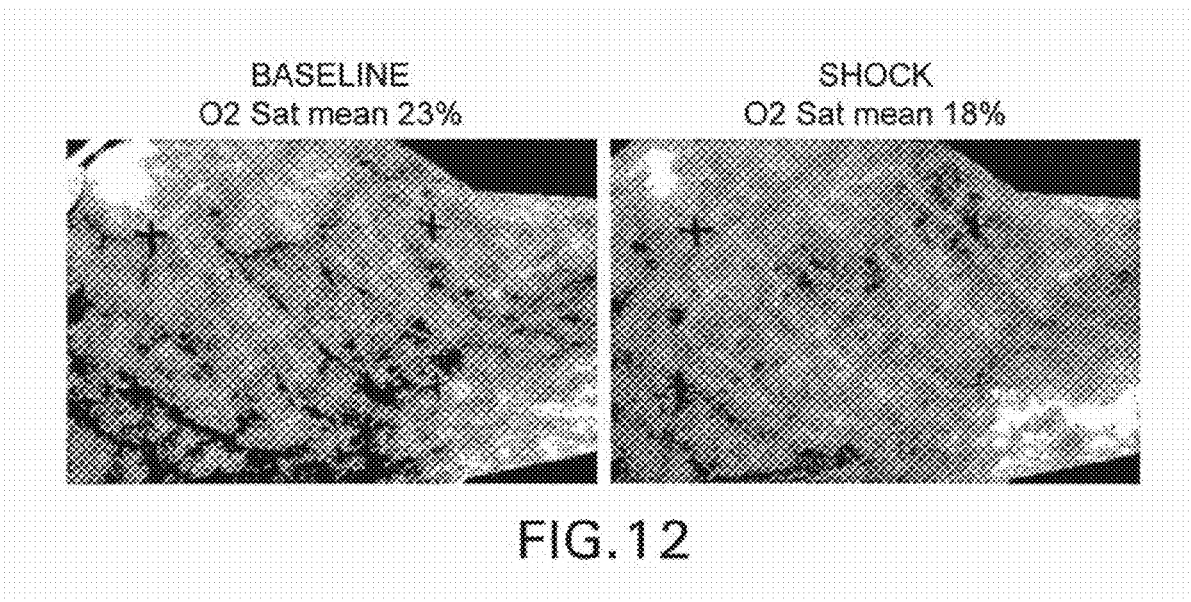
FIG. 12 MHSI $S_{HSI}O_2$ reveals changes in circulatory patterns that are indicative of patient survivability. Comparing the baseline (left panel) to the shock image (right panel) of $S_{HSI}O_2$ shows development of a "feathery" pattern. This pattern developed in many of the animal subjects that either died during the procedure or did not exhibit strong recoveries to the test procedure, and appears to indicate a higher likelihood of an unfavorable outcome.

The feathery pattern seen in FIG. 12 can be detected by using image processing approaches to detect edges and features in the image that may be "feathery". In addition to the methods characterizing mottling described above (spread value for different size ROI, area-to-perimeter ratio, ratio of short to long axis in the mottling blob), another possible implementation can be applied. An image template can be constructed that resembles either the entire feathery feature, or a sub-section of it (for example, a single branching). Scaled and rotated versions of this template can be correlated against the hyperspectral image to generate "match" scores. Presence of high match scores in a region of the image can be taken to be an indication of the presence of "feathering" in the image, and will result in an alert being given to the medical personnel. This image processing approach is similar to that described by Delanoy et al. but has not been previously applied to hyperspectral detection of shock, assessment of survivability, assessment of adequacy of resuscitation or other evaluation of physiologic state.

The following examples illustrate embodiments of the invention, but should not be viewed as limiting the scope of the invention.

EXAMPLES

First a target ROI is selected, preferably this is localized tissue, and more preferably a patch of skin and most preferably a patch of skin that is relatively hairless and relatively flat such as the forearm. Other potential sites of preference include the cheek, thigh, deltopectoral region. In an alternate embodiment, the localized tissue is buccal mucosa, rectal mucosa, bladder mucosa, intra abdominal serosa or other tissue available for imaging. We then collect spectral data from the ROI or a portion of the ROI at a pre-specified distance or at a distance that is measured or estimated or recorded. Preferably this is less than 10 feet and more preferably between six and 36 inches, and most preferably between 12 and 18 inches.

In another embodiment, the preferred distance is between 0.1 and 6 inches, more preferably between 0.5 and 2 inches. In another embodiment, the preferred distance is between 10 feet and 1000 feet, more preferably between 10 and 300 feet and more preferably between 10 and 100 feet. In each instance, preferably adjustment of the optics to provide the appropriate resolution is undertaken. Preferably data is collected with automatic zoom optics. In another embodiment a fixed focal length is required by the system. In another embodiment manual adjustment of the optics is utilized to obtain the desired field of view and resolution for the image. Preferably, prespecified optical settings are used or the automatically or a manually selected optical setting is measured or estimated or recorded either automatically or manually. Preferably image stabilization methods are utilized. One or a series of images is obtained. If more than one image is obtained, sequential images can be collected at a prespecified interval, or at an interval that is measured or estimated or recorded. Preferably sequential measurements will be collected at between 10 milliseconds and one hour. More preferably measurements will be collected at between 10 millisecond and 10 minute intervals. Most preferably, measurements will be collected at between 10 milliseconds and 1 minute intervals. In another embodiment, measurements will be collected preferably between 1 millisecond and one minute, more preferably at between 1 milliseconds and 1 second.

Preferably the instrument is configured as a free standing device that is fixed to a moveable cart, table, wall or ceiling fixture. More preferably it is a small hand held device.

In another embodiment, it is in whole or in part mounted in or with other optical equipment such as binoculars or the sighting of a gun.

In another preferred embodiment, the device will be maintained in close approximation to the body. More preferably, the relationship between the device and the body will be maintained as relatively fixed. Most preferably, a nonconstrictive band can fix a portion of the device in a position above the skin for continuous or intermittent readings.

Relevant spectral data is collected from one or more images of the ROI. Preferably between 1 and 1000 wavelength bands are collected, more preferably between 2 and 100 bands and yet more preferably between 2 and 60 bands and most preferably between 2 and 25 bands. In another embodiment, preferably between 2 and 10 bands are collected and more preferably between 3 and 5 bands are collected. Preferably the spectral region from which data is collected is between 450 and 1200 nanometers.

Hemorrhagic Shock

Changes in cutaneous oxygen saturation ($S_{HSI}O_2$) following chest trauma and hemorrhage were observed which were not evident to the naked eye, but which produced hyperspectral images with a pronounced mottling pattern. Image intensity of $S_{HSI}O_2$ images of the skin decreased during hemorrhagic shock in a porcine model, indicating a decrease in oxygen saturation in the skin.

Seventeen female Yorkshire pigs (9 in the hemorrhage group and 8 in the control group), weighing 36.4±0.11 kg were used. The animals were quarantined for one week and were fasted overnight prior to the procedure.

Animals were premedicated with 250 mg IM Telazol. After induction of anesthesia with isoflurane delivered through a mask, they were incubated, and were placed on a Datex-Ohmeda anesthesia ventilator with a tidal volume of 10 ml/kg and a respiratory rate of 12/min. The rate was adjusted to achieve normocapnea ($PaCO_2$=35-45 mm Hg). Anesthesia was maintained with a mixture of isoflurane (2-2.5%) and room air. Percutaneous sheath introducers were inserted into the carotid artery and external jugular vein bilaterally, and a 10 F Foley catheter was inserted into the urinary bladder. A splenectomy was performed via a midline laparotomy. The splenic artery was tied off before splenectomy to allow drainage of blood from the spleen into the circulation. An infusion of lactated Ringer's solution (LR) at 1.5 times the spleen weight was administered immediately after the splenectomy. At the end of surgery the isoflurane was decreased to 0.6% and an infusion of ketamine (250-350 µg/kg/min) was begun. The ketamine-isoflurane anesthesia was continued until the end of the study. Depth-of-anesthesia assessment and anesthetic dose adjustments were made as needed. Core temperature was maintained between 37-39° C. by means of an external heating pad.

A flow-directed pulmonary artery catheter was inserted via the external jugular vein introducer sheath to permit measurement of mixed venous blood gases and core temperature. One of the carotid arterial introducer sheaths was used for measurement of the arterial blood pressure (ABP). Clinical pressure transducers were used. The heart rate was obtained from the electrocardiogram. Regional skin temperature was monitored on both hind limbs using thermocouples.

After a postoperative stabilization period (1-2 hours), baseline data were collected. The animals in the hemorrhage group (HEM, n=9) then underwent withdrawal of blood through the carotid line with a syringe. Three withdrawals, each 10 ml/kg, were performed at a constant rate of 1 ml/kg/min. Blood was collected into a bag containing CPDA anticoagulant. Each of the three 10-min hemorrhage periods was followed by a 15-min observation period. Following the third observation period, the animals were resuscitated with intravenous infusion of LR at 1.5 times the shed blood volume. The duration of the LR resuscitation period was 25 min. Additional fluid to exceed the initial resuscitation volume was then administered as needed to return the heart rate and blood pressure toward baseline values. The 25-min LR infusion period was followed by a 30-min observation period, and then a 25-minute period during which the shed blood was reinfused. The animals were observed for an additional hour thereafter and then were euthanized. Blood and LR were infused using a fluid warmer. HSI images were obtained of the inner hind limb throughout.

Animals in the control group underwent similar surgical preparation and received a maintenance LR infusion at 100 ml/hour. Data were obtained at the following time points: baseline, after each 10 ml/kg blood withdrawal, after LR resuscitation, and after blood reinfusion.

Blood withdrawal resulted in an early drop in systolic arterial pressure, which became statistically significant during the first withdrawal, and which remained decreased until after LR resuscitation. Heart rate increased with blood withdrawal, although in delayed fashion—becoming significant only during the second bleed; it returned to control levels after reinfusion of shed blood.

All HEM animals showed a decrease in mean $S_{HSI}O_2$ with blood loss; these changes became significant after the $3^{rd}$ bleed. They were evident on the gray scale $S_{HSI}O_2$ pictures, but not to the naked eye. Decreases in HSI OxyHb, as well as in arterial base excess and mixed venous saturation of oxygen, were significant after the $2^{nd}$ bleed. These changes were all reversed by resuscitation.

The mean intensity of both $S_{HSI}O_2$ and OxyHb images of the skin, obtained by hyperspectral imaging in the visible wavelength range, decreased during hemorrhagic shock and were restored during resuscitation in the anesthetized pigs. These changes roughly paralleled those observed in several invasively obtained variables, to include the systolic arterial pressure, the arterial base excess, and the mixed venous saturation of oxygen. However, the lack of tight correlation is expected, given that HSI provides additional information about hemodynamics and physiologic condition and may be associated with HSI providing earlier information as to hemodynamic compromise and impending collapse.

FIG. 5 shows data results from an example porcine subject. Histograms are formed for hyperspectrally-calculated images of oxygen saturation taken at baseline and during shock. The histograms show that the mean value of the oxygen saturation provides a cue as to circulatory shock for this subject.

Oxygen saturation images in which the brightness of each pixel is proportionate to the intensity of the $S_{HSI}O_2$ for that pixel. Both baseline images, and images obtained during the third post-bleed period, are included. The decrease in image intensity is evident on these images. Qualitatively, some animals, but not all, demonstrated an increase in mottling during shock, also evident on the oxygen saturation images. Neither of these changes was evident to the naked eye. Quantitatively, the mean-gray-scale intensity for these $S_{HSI}O_2$ images decreased linearly with blood withdrawal, becoming significantly decreased in comparison with control animals after the third bleed, and restored to control levels by resuscitation.

The mean value of the OxyHb fit coefficient for the ROI also decreased linearly with hemorrhage, but it showed an earlier statistically significant decrease, after the second bleed, which was also restored by resuscitation. Meanwhile, the mean DeoxyHb fit coefficient for the ROI appeared to trend upward during and after the third bleed, but these changes were not significant. As a rough index of the degree of mottling present, the standard deviation of the gray-scale histogram of the oxygen saturation images appeared to increase with hemorrhage, but this was not statistically significant. Laser Doppler imaging demonstrated a linear decrease in skin blood flow for the ROI with blood loss, which became significant after the third bleed and which was reversed by resuscitation.

Linear regression was performed to examine the possible relationship between mixed venous saturation of oxygen and $S_{HSI}O_2$. This analysis demonstrated a linear relationship, with a relatively low $r^2$ of 0.12 (p<0.001, df=114). Correlation with the systolic arterial pressure was similar ($r^2$=0.14, p<0.001, df=202). Although the laser Doppler image intensity appeared to follow a time course similar to that of $S_{HSI}O_2$, there was no relationship between the 2 variables on linear regression ($r^2$=0.01, p=0.312, df=112).

The shock monitoring approach described in this patent utilizes hyperspectral imaging. In this technique, a two dimensional image is created that has spectral data inherent in each individual pixel. In a preferred embodiment, the spectrum of each pixel is correlated with the presence and concentration of various chemical species. This data is interpreted as the abundance of these species in a surface. This has a high correlation with various physiologic conditions and offers the possibility of improved metabolic monitoring (FIG. 11).

Several types of response to shock that were observable using hyperspectral imaging (as seen in the hypovolemic shock in porcine subjects). First, the overall oxygenation levels (or oxygen saturation) were seen to decrease in many subjects. Second, a mottled appearance was seen in the skin of several subjects. This is a known indicator of shock and results from a change in the micro-circulatory patterns of blood flow as the body attempts to compensate for the event causing physiological stress. Finally, a distinctive change in circulatory patterns may occur, resulting in a "feathery" pattern (FIG. 12). These changing circulatory patterns appear to correlate with poor outcomes, and therefore provide a measure of the likelihood that the patient is moving into an irreversible shock.

Figure 13A:
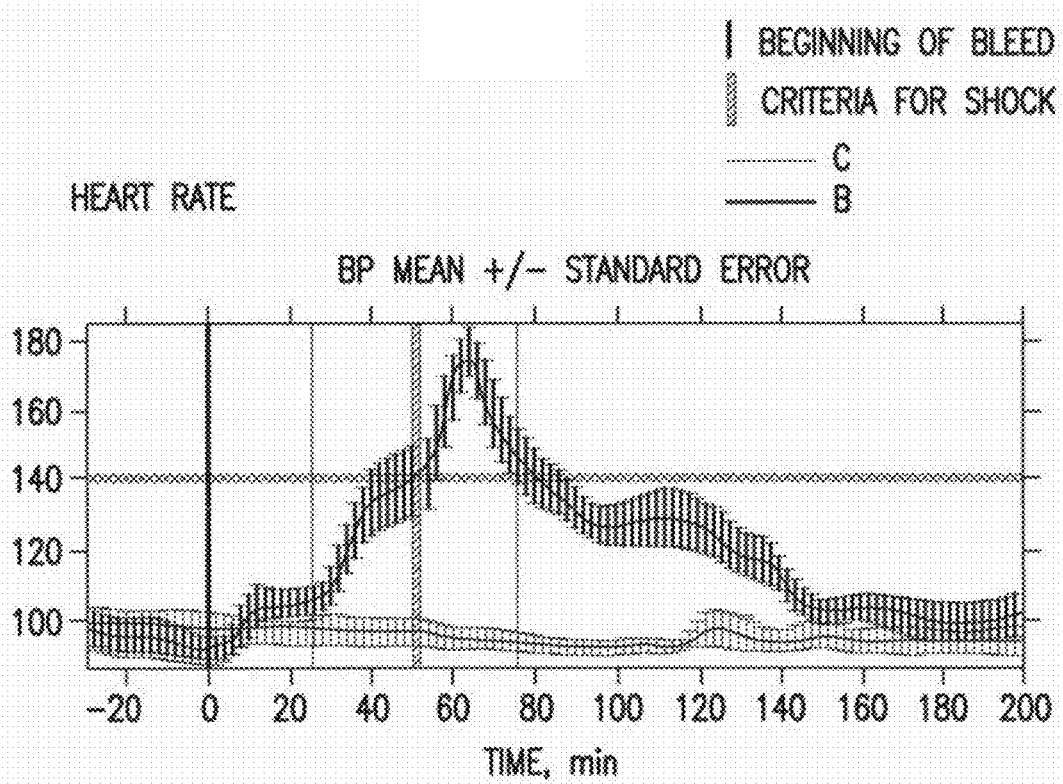
FIG. 13 The mean values for physiological and hyperspectral parameters as a function of time together with the standard error for each time step is provided. The heart rate and blood pressure are shown in FIGS. 13A and 13B, respectively. The results using mean, spread, blobbiness, and temporal shift methods are shown in FIGS. 13C through 13F, respectively.
Figure 13B:
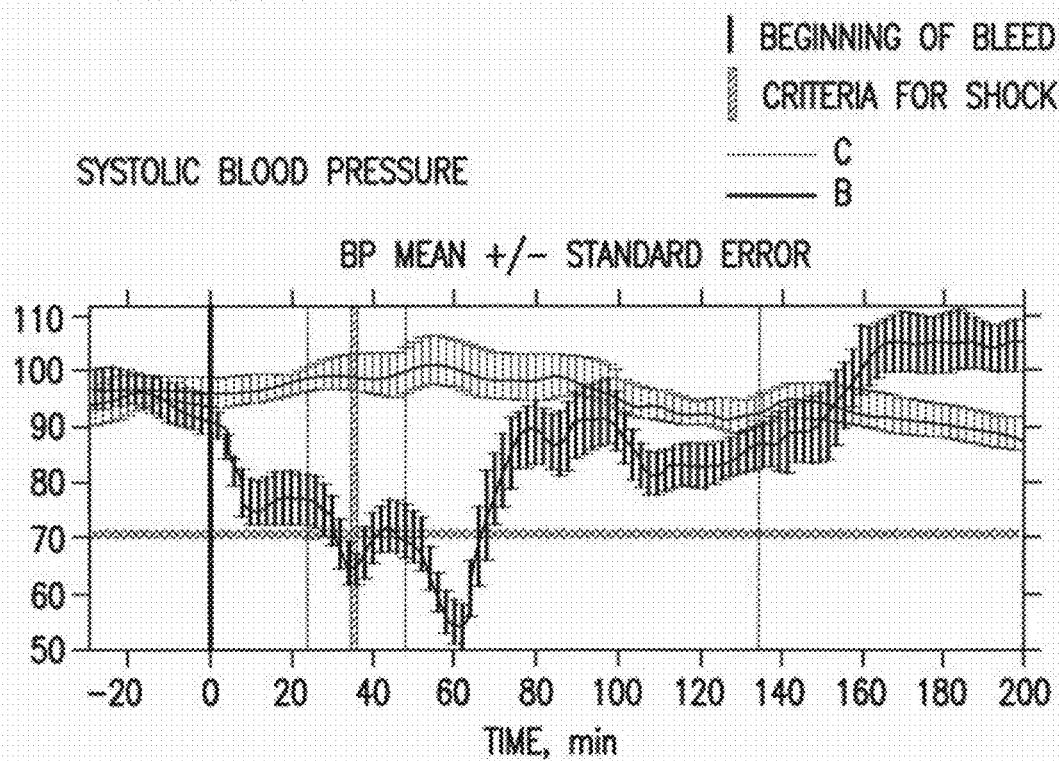
Figure 13C:
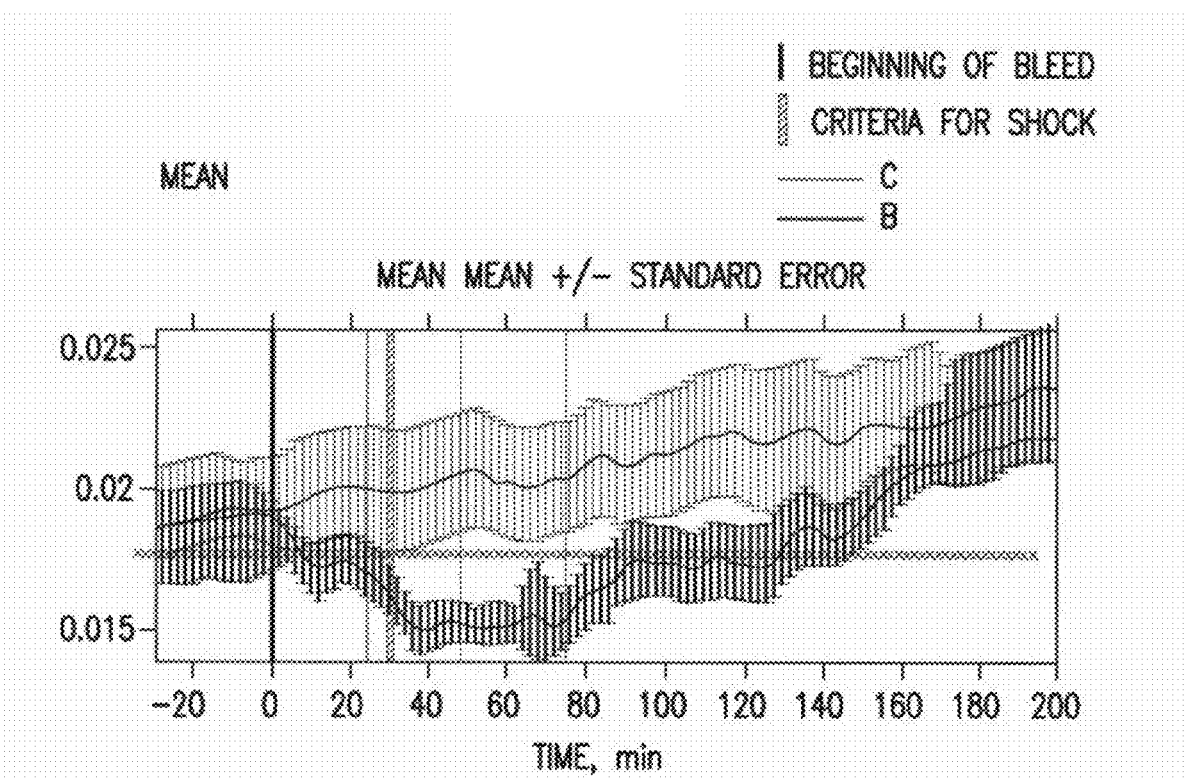
Figure 13D:
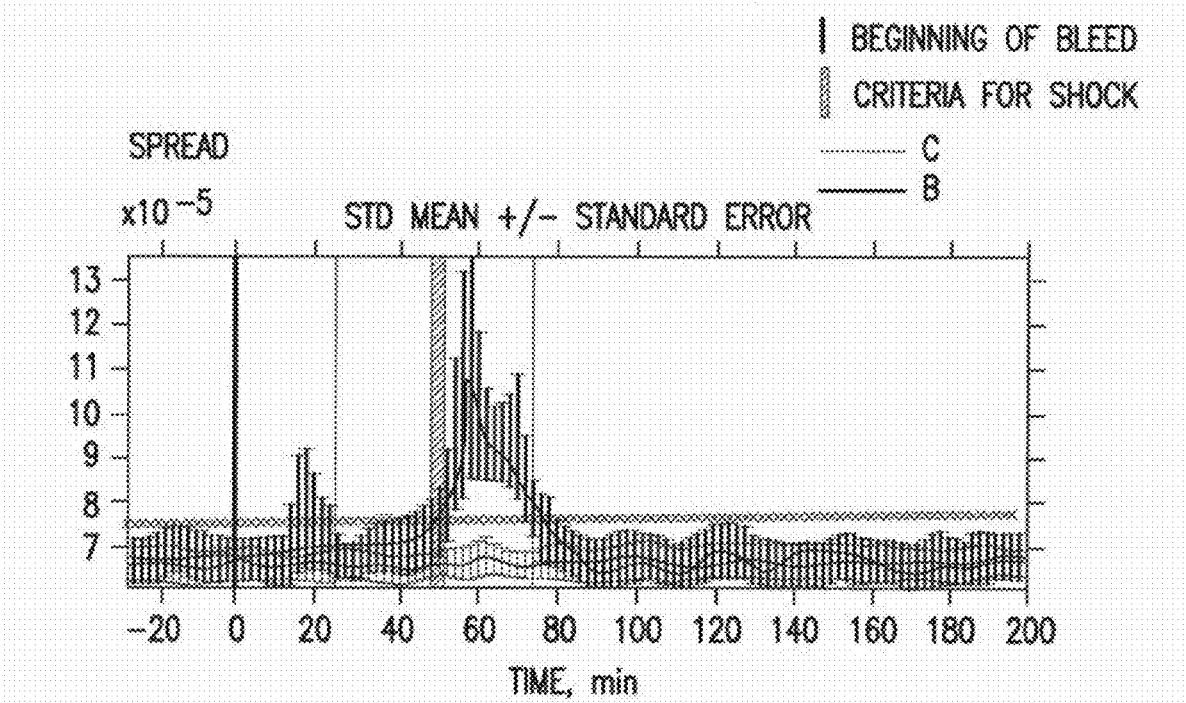
Figure 13E:
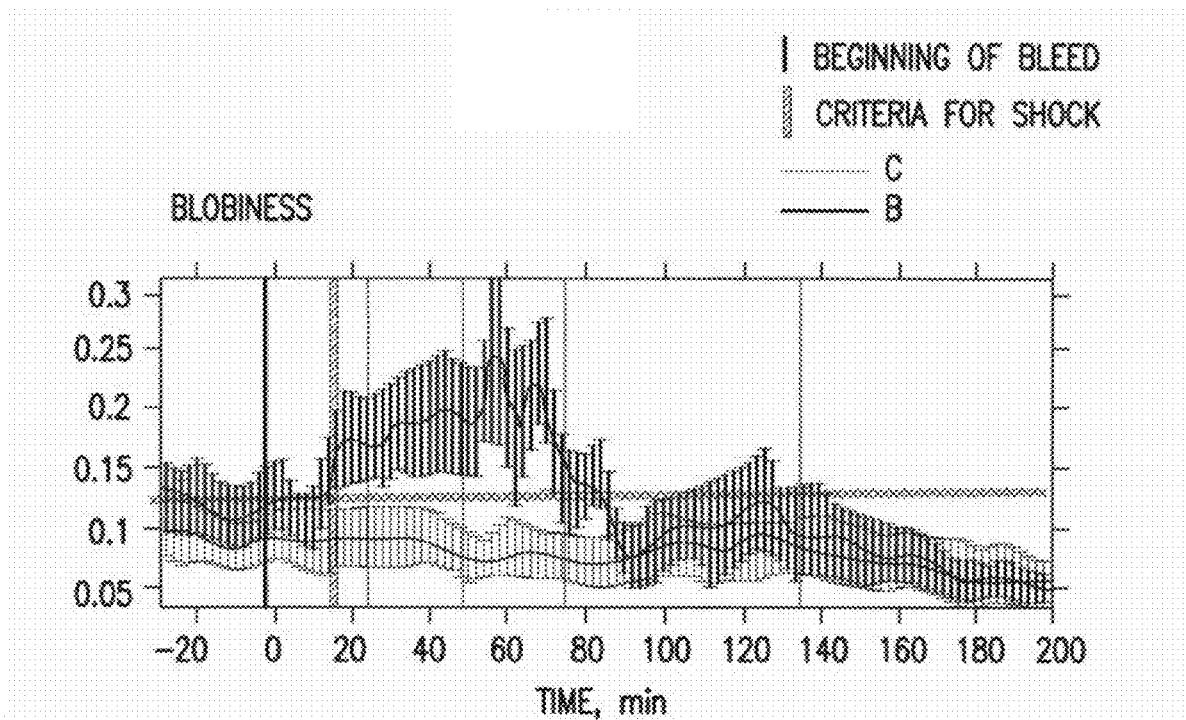
Figure 13F:
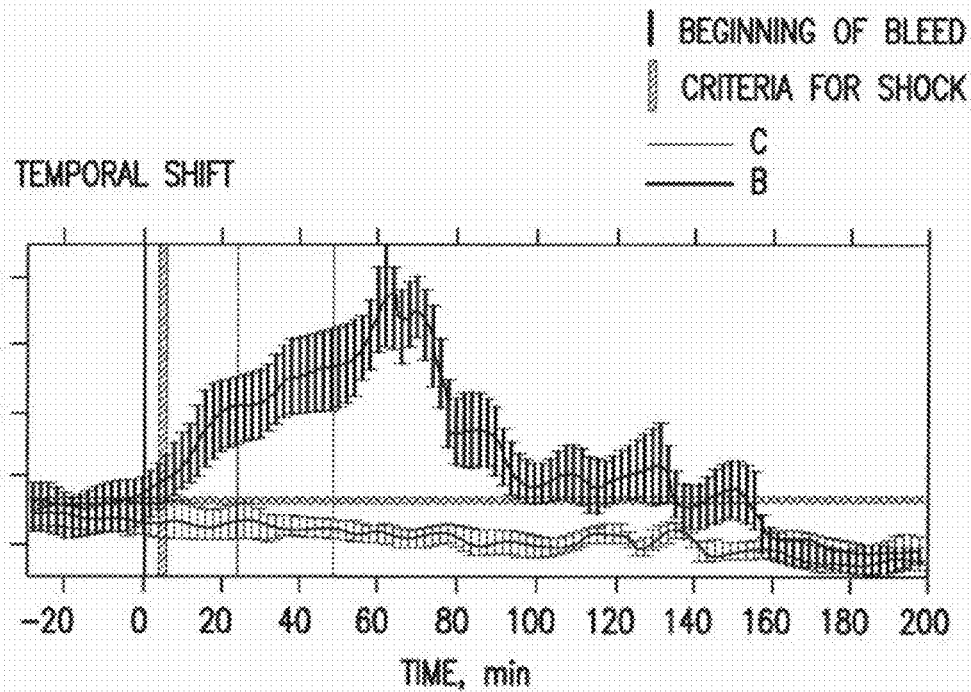
Figure 14:
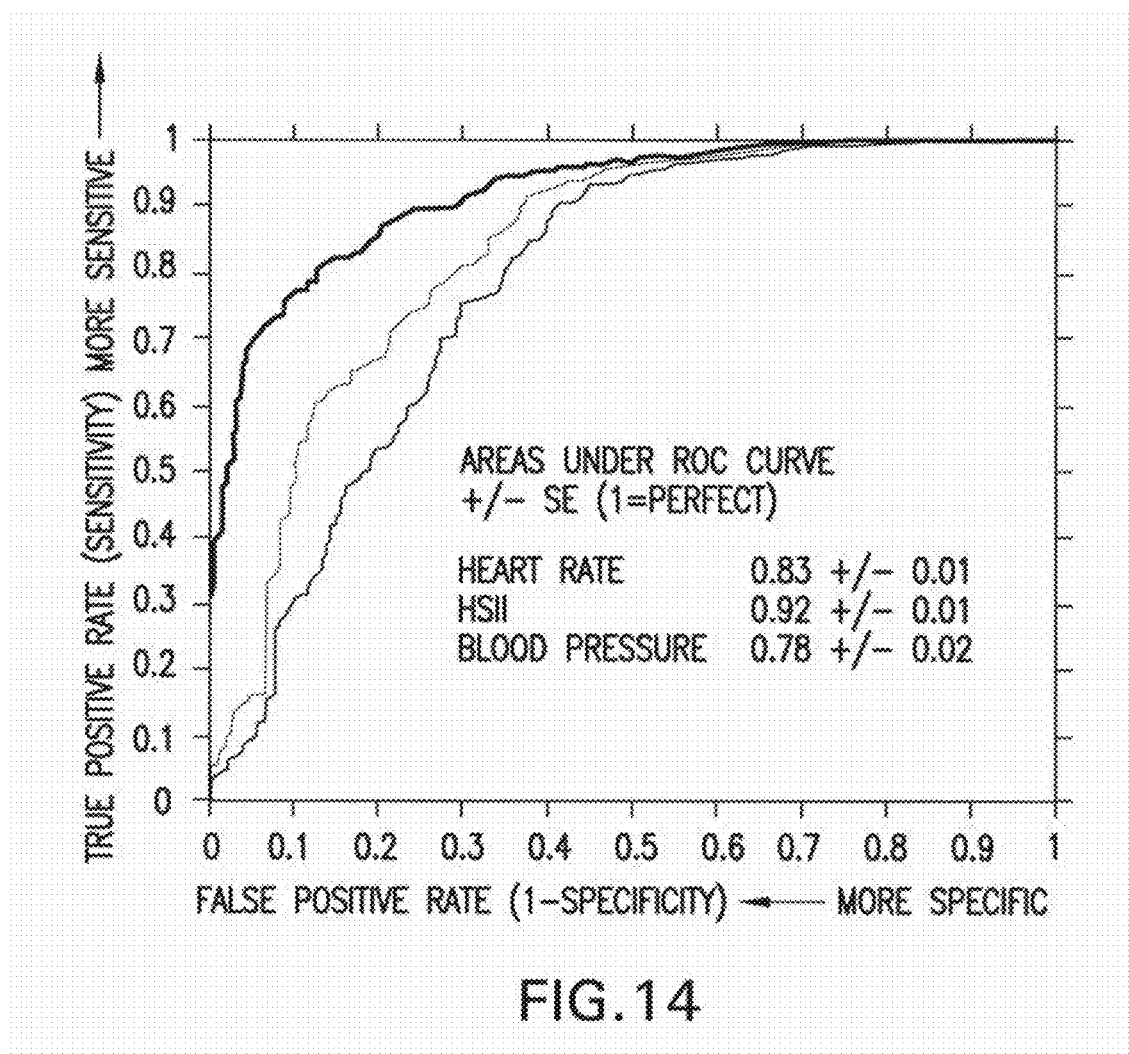
FIG. 14 Receiver Operator Characteristic (ROC) curves and area under ROC curves with standard error for the heart rate, systolic arterial blood pressure, and hyperspectral shock index, HSSI.

HSSI is a non-linear combination of 4 scalar factors that were derived with image processing techniques applied to the hypercubes for each animal at every time step. Two of the factors (MEAN and SPREAD) are based on analysis of the entire region of interest (ROI). The other 2 factors (blobbiness "BLOBS" and temporal shift "TEMPORAL") are based on feature analysis that identifies patterns of oxygenation of the tissue, its amplitude, lateral extension and frequency of change. To summarize data from all 14 subjects, we displayed mean values for physiologic (HEART RATE and SYSTOLIC BLOOD PRESSURE, FIGS. 13A and 13B) and hyperspectral parameters (MEAN, SPREAD, BLOB and TEMP, FIGS. 13C through 13F) as a function of time together with the standard error for each time step. Here, blue lines represent the 6 control subjects and black lines the 8 bleed subjects. If we use a heart rate of 140 (.about. human 110) as the metric for shock, we see this event at about. 50 minutes after the first bleed. If we use a systolic blood pressure of 70 (.about. human 100) as the metric for shock, we see this event at 35 minutes after the first bleed. Using a HyperSpectral Shock Index (HSSI) of >1, significant bleeding is indicated 5 min into the first bleed. To avoid dependency of the comparison on a threshold value, we constructed Receiver Operator Characteristic (ROC) curves that evaluate sensitivity and specificity in identifying shock by three parameters: HEART RATE, SYSTOLIC BLOOD PRESSURE, and HSSI (FIG. 14).

Battlefield

Hyperspectral or multispectral imaging is useful as small, portable noninvasive monitoring devices for use by first responders in a battlefield or emergency room setting. The responder captures hyperspectral or multispectral data from the patient. Software built into the device provides the responder with an assessment of the patient's state, including likelihood of the patient entering a state of shock as well as any available indicators of likely outcome. This information is used by the responder in determining the appropriate level of care needed to stabilize the patient.

In one exemplary embodiment, the battlefield/first responder system for simultaneous collection and integration of both visible and near-infrared MHSI data is built in a rugged enclosure. The visible and NIR systems each consists of three functional modules—a Spectral Imager (SI), supporting Controller and Power Module (CPM) and Control and Data Acquisition Computer (CDAC). The spectral imagers consists of a visible and NIR liquid crystal tunable filters (LCTFs) and complementary metal oxide semiconductor (CMOS) visible and NIR imaging sensors, fitted with macro lenses. Preferably, the LCTFs have a bandwidth of 9 nm, more preferably, 8 nm, and most preferably 7 nm. By varying the voltage across the LCTF, the wavelength of light admitted through the LCTF, and into the camera, can be varied. The focal plane of the system is defined at the point of intersection of two crossed laser pointers. The imaging sensors are composed of 1280 pixels×1024 pixels. The system preferably has a working focal length of approximately 12 inches and a field of view of approximately 7 cm×6 cm, corresponding to approximately 60 μm resolution.

In another embodiment, only visible light is used.

In another embodiment, only NIR light is used.

In another embodiment visible light and LCTF and single or only several NIR bands are collected through a simplified filter system.

Energy efficient light emitting diodes (LEDs) are used to illuminate the tissue surface. Preferably, eight, more preferably, 6, and most preferably, four visible LEDs are used to deliver 1.8 W of broadband light between preferably 300-970 nm, more preferably, 400-850 nm, more preferably, 450-800 nm, more preferably 450-750 nm, and most preferably 450-720 nm. NIR emitters at 740, 780, 810, and 970 nm with 30 nm bandwidths are used to deliver 5 W of broadband NIR light between 720-830 nm and 945-1000 nm. A single hyperspectral cube consists of images at 25 visible and 25 NIR images. The integration times of each image is adjusted such that the brightest area in the image filled approximately 80% of the full well capacity of the CCD. A complete spectral datacube is collected in under one minute.

Another embodiment uses ambient light such as sunlight or ambient light either alone or supplemented with another independent light source such as a flashlight. In this embodiment automatic calibration is undertaken by the system which can measure the flashlight output and/or ambient lighting and calibration effected or instructions given for the operator to make adjustments to the system.

The data is then converted to optical density units by ratioing the sample data to data acquired from the white reflectance standard using a Beer's Law algorithm. Reference oxyhemoglobin and deoxyhemoglobin spectra are obtained in electronic format. A four-term linear regression fitting of oxyhemoglobin, deoxyhemoglobin, offset and slope terms are then performed on each of the spectra in the image cube. The regression fit coefficients are then used to calculate a relative oxygen saturation percentage for each spectrum in the image cube:

$$S_{HSI}O_2 = OxyHb/(OxyHb+DeoxyHb)*100,$$

where OxyHb is the fit coefficient for oxyhemoglobin, and DeoxyHb is the fit coefficient for deoxyhemoglobin, resulting from the linear regression.

The state of shock is then assessed by evaluating the levels of oxy and deoxyhemoglobin, total hemoglobin and hemoglobin oxygen saturation. The spatial distribution or mottling pattern observed in oxygenation is further used to refine class distinctions. Additional refinement is made by observing how the mottling pattern changes over time.

In one exemplary example, MHSI can be used to monitor a subject during biological or chemical exposure even in cases where access to the victim is difficult due to the victim wearing a protective suit. As demonstrated in FIG. 15, hyperspectral imaging of the face can be acquired directly through the protective goggles.

Hypothermia

Four animals weighing 36.2±0.45 kg were used to evaluate the effect of systemic hypothermia on the hyperspectral images. These animals underwent similar surgical preparation to those in the hemorrhage study. After baseline data were obtained, the animals were continuously cooled down over 1 hour 40 min by placement between 2 cooling blankets set at 4° C., followed shortly thereafter by covering the head, neck, axillas, and torso with plastic bags filled with ice.

In 3 animals, the target core temperature was 31° C. The duration of cooling was intended to approximate the duration of the 3 consecutive bleed and observation sessions described for the hemorrhage protocol. To avoid decreasing the core temperature below 31° C., the blanket and room temperature were set to 42° C. and 30° C. respectively once the core temperature reached 33° C. The ice packs were then removed, and a Bair Hugger warming blanket was added. Rewarming was carried out until baseline core temperature values were reached. Body temperature was monitored via pulmonary artery catheter and rectal temperature probe. Regional skin temperature was monitored on both hind limbs using thermocouples.

Because the skin $S_{HSI}O_2$ did not appear to change at core temperatures as low as 31° C., a fourth animal was cooled further to 22° C., without rewarming.

In other preferred embodiments, the assessment of shock can be determined using standard classification methods such as discriminant analysis or classification trees. Analysis can start using the diffuse reflectance signal collected with the camera before or after converting to optical density units. The method can also use principal component analysis or some other means for data reduction prior to analysis.

The present invention provides a hyperspectral/multispectral imaging system which demonstrates changes in local tissue that reflect changes in systemic physiology, here changes in skin oxygenation and s $S_{HSI}O_2$ during hemorrhagic shock and resuscitation. Other preferred uses of HSI include, but are not limited to, the macroscopic distribution of $S_{HSI}O_2$, the in-situ detection of tumor during breast cancer resection in rat, the determination of tissue viability following plastic surgery and burns, claudication and foot ulcers in peripheral arterial disease patients and diabetic patients, and applications to hypovolemic decompensation and circulatory collapse under lower body negative pressure (LBNP) in pigs and humans, respectively.

Throughout the application, where we have described hyperspectral imaging, multispectral imaging could be similarly employed and reference to MHSI or HSI includes reference to either hyperspectral or multispectral imaging.

While these methods and instruments are described for application to medicine and physiology, assessments, they can be similarly used in other application areas including in vivo and invitro biological, forensic, environmental, geological, chemical, astronomical and other areas.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference, including U.S. patent application, "Medical Hyperspectral Imaging for Evaluation of Tissue and Tumor, filed Nov. 29, 2005 (Application No. to be assigned). It is intended that the specification and examples be considered exemplary only with the true scope and spirit of the invention indicated by the following claims.

The invention claimed is:

1. An apparatus for evaluating a local tissue of a subject, the apparatus comprising:
   an optical acquisition system configured to generate medical hyperspectral imaging data of a region of interest of the subject, wherein the optical acquisition system has a first field-of-view;
   a diagnostic processor that receives the medical hyperspectral imaging data from the optical acquisition system;
   at least one algorithm running on the diagnostic processor, wherein the at least one algorithm uses at least one of oxygenated, deoxygenated, and total hemoglobin levels based on the medical hyperspectral imaging data to quantify a clinical signal of the local tissue of the subject;
   a display device configured to display the quantified clinical signal of the local tissue of the subject; and
   an image projector having a second field-of-view that is precisely co-aligned with the first field-of-view, wherein the image projector projects a fiducial self-calibration pattern and the generated medical hyperspectral imaging data onto the region of interest in a visible spectrum wavelength range, wherein
   the optical acquisition system is configured to read the fiducial self-calibration pattern projected onto the region of interest in order to achieve co-registration between the first field of view and the second field of view and map the generated medical hyperspectral imaging data onto the region of interest.

2. The apparatus of claim 1, wherein the optical acquisition system comprises a digital camera that comprises a charge-coupled device element and a lens.

3. The apparatus of claim 1, wherein the optical acquisition system comprises a visible-wavelength, liquid-crystal tunable filter.

4. The apparatus of claim 1, wherein the optical acquisition system comprises a NIR-wavelength, liquid-crystal tunable filter.

5. The apparatus of claim 1, wherein the optical acquisition system comprises a filter that has the capacity to filter both visible and NIR light.

6. The apparatus of claim 1, wherein the optical acquisition system comprises a visible filter and an NIR-wavelength, liquid-crystal tunable filter.

7. The apparatus of claim 1, wherein the optical acquisition system comprises a visible-wavelength, liquid-crystal tunable filter and a narrow band IR illumination source.

8. The apparatus of claim 1, wherein the optical acquisition system comprises a visible-wavelength, liquid-crystal tunable filter and one or more infrared filters.

9. The apparatus of claim 1, wherein the optical acquisition system comprises a digital camera having a CMOS element and a lens.

10. The apparatus of claim 1, wherein the optical acquisition system comprises an acousto-optical tunable filter.

11. The apparatus of claim 1, wherein the optical acquisition system comprises a switchable filter array.

12. The apparatus of claim 1, wherein the optical acquisition system comprises a filter, wherein one or more selected wavelengths of light are delivered from a light source into the filter.

13. The apparatus of claim 12, wherein the one or more selected wavelengths of light comprise NIR wavelengths.

14. The apparatus of claim 12, wherein the one or more selected wavelengths of light comprise visible wavelengths.

15. The apparatus of claim 12, wherein the one or more selected wavelengths of light comprise visible wavelengths and NIR wavelengths.

16. The apparatus of claim 12, comprising a filter coupled to a front of the optical acquisition system.

17. The apparatus of claim 1, wherein the optical acquisition system comprises a power supply and an illuminator that supplies coaxial or near-coaxial illumination, the power supply powering the illuminator.

18. The apparatus of claim 1, further comprising a software program configured to control the diagnostic processor.

19. The apparatus of claim 1 wherein the apparatus is portable.

20. The apparatus of claim 1 wherein the acquisition of medical hyperspectral imaging data by the optical acquisition system is performed in real-time or near real-time.

21. The apparatus of claim 1, wherein the optical acquisition system comprises at least two optical stages.

22. The apparatus of claim 1, wherein the optical acquisition system comprising at least one polarizer.

23. The apparatus of claim 1, wherein an outputted status of the subject, by the display device, comprises a visual signal.

* * * * *